US008518662B2

(12) United States Patent
Ritzen et al.

(10) Patent No.: US 8,518,662 B2
(45) Date of Patent: *Aug. 27, 2013

(54) DISPOSABLE CASSETTE AND METHOD OF USE FOR BLOOD ANALYSIS ON BLOOD ANALYZER

(75) Inventors: Kalle Ritzen, Vattholmasvägen (SE); Ingemar Berndtsson, Borevägen (SE); Björn Roos, Torsgatan (SE); Gunnar Magnusson, Marviksvägen (SE)

(73) Assignee: Boule Medical AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 13/544,079

(22) Filed: Jul. 9, 2012

(65) Prior Publication Data
US 2012/0276582 A1 Nov. 1, 2012

Related U.S. Application Data

(63) Continuation of application No. 12/270,083, filed on Nov. 13, 2008, now Pat. No. 8,247,191.

(51) Int. Cl.
| | |
|---|---|
| *C12Q 1/24* | (2006.01) |
| *C12M 1/34* | (2006.01) |
| *C12M 3/00* | (2006.01) |
| *C12M 1/00* | (2006.01) |
| *C12N 11/00* | (2006.01) |
| *C25B 9/00* | (2006.01) |
| *C25B 11/00* | (2006.01) |
| *C25B 13/00* | (2006.01) |
| *G01N 1/00* | (2006.01) |
| *G01N 27/26* | (2006.01) |
| *G01N 31/00* | (2006.01) |
| *G01N 33/50* | (2006.01) |
| *G01N 33/487* | (2006.01) |

(52) U.S. Cl.
USPC ... 435/30; 435/287.1; 435/287.6; 204/403.02

(58) Field of Classification Search
None
See application file for complete search history.

(56) References Cited

U.S. PATENT DOCUMENTS

| | | | |
|---|---|---|---|
| 5,652,149 A | 7/1997 | Mileaf et al. | |
| 5,863,502 A | 1/1999 | Southgate et al. | |
| 7,335,339 B2 | 2/2008 | Berndtsson | |
| 8,247,191 B2 * | 8/2012 | Ritzen et al. | 435/30 |
| 2006/0013740 A1 | 1/2006 | Berndtsson et al. | |

FOREIGN PATENT DOCUMENTS

| | | |
|---|---|---|
| WO | 2004/045770 | 6/2004 |

OTHER PUBLICATIONS

International Search Report; PCT/SE2009/051262, dated Feb. 17, 2010.

* cited by examiner

*Primary Examiner* — Chris R Tate
*Assistant Examiner* — Russell Fiebig
(74) *Attorney, Agent, or Firm* — Latimer IP Law, LLC

(57) ABSTRACT

A disposable cassette for blood analysis includes a housing having an upper panel and a sampling section having a filling inlet; at least one pair of chambers in a form of depression of the upper panel of the housing and sealed by a diaphragm; portions of the diaphragm over the chambers being flexible; and one or more channels adapted to interconnect the pair of chambers; one of the chambers containing a predetermined amount of a reagent for blood analysis; and a sample outlet disposed next to and connected to the chamber containing the reagent, the sample outlet including an outlet cavity recessed from the upper panel, a divider disposed therein, and a cover covering the outlet cavity; the sample outlet sealing the reagent to the chamber containing the reagent. Further disclosed is the method of using the disposable cassette for measurements of hematology parameters on a blood analyzer.

20 Claims, 13 Drawing Sheets

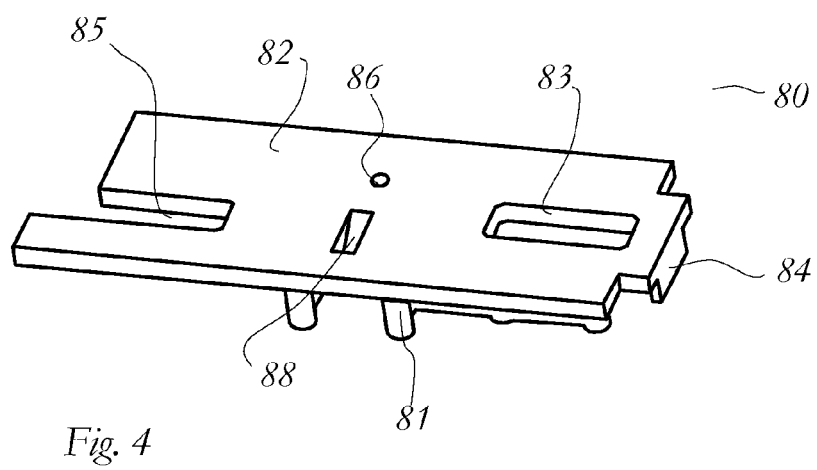
Fig. 4
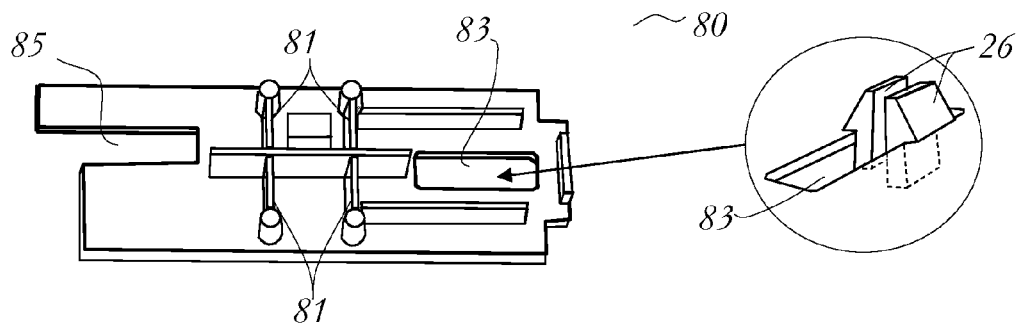
Fig. 4A
Fig. 4B

DISPOSABLE CASSETTE AND METHOD OF USE FOR BLOOD ANALYSIS ON BLOOD ANALYZER

CROSS REFERENCE TO RELATED APPLICATION

This application is a continuation of U.S. patent application Ser. No. 12/270,083, filed Nov. 13, 2008, which is hereby incorporated by reference in its entirety.

BACKGROUND OF THE INVENTION

1. Field of the Invention

The present invention relates to a disposable cassette and method of use for measurement of blood samples on a blood analyzer.

2. Discussion of Related Art

Various hematology analyzers are commercially available, from the high end, high capacity and high speed, fully automated instruments in hospitals to the low end, small counter top instruments for doctor's offices. Almost all of these instruments have multiple reagents and cleaner on board for automated sample preparation and measurements on the instruments. Although these hematology analyzers have known advantages of high capacity, batch sample analysis, automated sample aspiration and preparation, and automated cleaning cycles, these instruments are relatively high cost and use large quantity of reagents, which requires high maintenance of the instruments and reagent inventory management. Therefore, it is difficult to adapt these instruments in a near-patient test environment, such as in the emergency room, where minimum maintenance, minimum personal training and operator skill are required.

In the recent years, disposable cassette containing reagents for one sample analysis and blood analyzers adapted to use the disposable cassettes have been developed for meeting such a need in near-patient testing.

U.S. Pat. No. 7,335,339 discloses a disposable cassette which has a turning valve for sampling or isolation blood for different measurements and two cylinders containing pre-filled reagents for blood analysis. Mixing of the reagent with a blood is affected by a piston located in each cylinder. The structure of the cassette is complex and it is costly to manufacture. In this cassette, the pre-filled reagents are separated from other parts of the cassette by the turning valve, which is a moving component itself. The cassette does not contain a cleaner and the measurement devices on the instrument are cleaned by a cleaning solution provided to the instrument.

WO 2004/045770 A1 discloses a disposable cassette, which includes multiple receptacles formed by depressions of a surface of the housing and sealed by a diaphragm, and multiple channels interconnecting selected receptacles. Two receptacles of the cassette contain a diluent, one receptacle contains a hemolysis agent, and another receptacle contains a cleaner, respectively. The cassette has an elongated hole adapted to receive a capillary holder specially designed to use with the cassette for receiving and holding a capillary tube or micropipette that is used to deliver a blood into the cassette. A portion of a blood is segmented by a sliding valve to mix with a first diluent to form a first diluted blood, then two portions of the diluted sample are segmented by the sliding valve, one is mixed with the second diluent to form a second diluted sample mixture for red blood cell measurement, and another is mixed with the hemolysis agent to form a lysed sample mixture for white blood cell measurement. The second diluted sample and the lysed sample mixture are withdrawn from the cassette through needles penetrating through sealed openings on two opposing sides of the cassette into a blood analyzer.

Despite the advantages of this cassette in its simple method of mixing by alternately applying a pressure on selected receptacles, it has several disadvantages rendering it difficult to use. This cassette lacks secure sealing of the liquid reagents during transportation. The liquid reagents are restricted from flowing into other sections only by the sliding valve, which itself is a moving component. The liquid reagents can easily leak out from the interface with the sliding valve, causes potential chemical contaminations to sliding valve that supposedly separates different portions of a blood to different reagents, and causes errors of the measurements, because the pre-filled reagents determine the ratio of a dilution and ultimately the concentrations of the blood cells to be measured.

Furthermore, this cassette requires two sequential steps of dilution, therefore, it consumes more diluent, and takes longer time to prepare the sample mixtures. As can be appreciated, accuracy of the measurements depends not only on the second step of mixing, but also on the completion and quality of mixing in the first dilution. Moreover, this cassette requires a special tool, the capillary holder, for filling the blood, which also increases the overall time for preparing the sample, as it requires operator to insert a glass capillary tube into the holder for each blood to be tested. It also increases the risk of injury, because the thin glass tube can be fractured when it is not aligned properly during insertion, and increases operator's exposure to bio-hazard materials. Additionally, this cassette requires a complex interface of the blood analyzer. Because withdrawing the sample mixtures is from two opposing sides of the cassette, the cassette has to be in a horizontal position with the device of applying pressures positioned above the cassette and the devices withdrawing the sample mixtures on both sides. Because of this structure, it is also difficult to avoid potential withdrawing air bubbles into the conduits connecting to the cell counting devices.

The inventors have determined that it is desirable to provide an improved disposable cassette that ensures sealing of the reagents contained in the cassette during storage and transportation to prevent cross-contaminations within the device and to improve accuracy of the blood measurements. It is further found to be desirable to have a cassette that provides a single step dilution for preparing sample mixtures for both red blood cell and white blood cell measurements with a simple process and shorter preparation time. Moreover, it is desirable to provide a cassette that can be supported by a simple interface of a blood analyzer. Furthermore, it is desirable to provide a cassette that is convenient and safe to use by the operators, and requires minimum training and skill.

SUMMARY OF THE INVENTION

In one aspect, the present invention is directed to a disposable cassette for blood analysis. In one embodiment, the disposable cassette comprises a housing having an upper panel with a sampling section having a filling inlet; at least one pair of chambers in a form of depression of the upper panel of the housing and sealed by a diaphragm; portions of the diaphragm over the chambers being flexible; and one or more channels adapted to interconnect the pair of chambers; one of the chambers containing a predetermined amount of a reagent for the blood analysis; and a sample outlet disposed next to and connected to the chamber containing the reagent. The sample outlet comprising an outlet cavity recessed from the upper panel, a divider disposed therein, and a cover covering the outlet cavity, and the sample outlet seals the reagent to the chamber containing the reagent. The disposable cassette also comprises a cleaner chamber containing a cleaning solution therein, and a cleaner outlet disposed next to and connected to the cleaner chamber. The cleaner outlet seals the cleaning solution to the cleaner chamber.

The disposable cassette further comprises a sampling sled disposed within the sampling section, slidable between a filling position and a flushing position. The sampling sled comprises a flat upper surface and a sampling cavity in a form of recess on the flat upper surface. When in the filling position, the sampling cavity is in fluid communication with the filling inlet, and when in the flushing position, the sampling cavity is in fluid communication with one or more channels adapted to interconnect the pair of mixing chambers.

In one embodiment, the diaphragm seals an upper side of the upper panel of the housing, and maintains a space between the diaphragm and the upper side of the upper panel above the vent opening. The cassette further comprises a vent lip elevated from the upper panel around the vent opening to maintain a distance between the diaphragm and the vent opening. Moreover, the cassette may further comprise a pair of electrodes disposed with the vent opening, with upper ends thereof positioned on the upper panel for electrical connection. The electrodes function as a blood sensor.

In a further aspect, the present invention is directed to a method of preparing a blood sample for measurements of blood cells using the disposable cassette of the present invention. The method comprises providing the disposable cassette described above; filling a blood sample through the filling inlet into the sampling section of the cassette; piercing the divider in the sample outlet by a piercing element and establishing fluid communication between the first chamber and a second chamber of the pair of chambers through one or more channels; isolating a volume of the blood sample using the sampling sled; applying a pressure on a portion of the diaphragm over the first chamber, and causing the reagent to flow through the sampling section, and flushing the isolated volume of the blood sample into the second chamber; and alternately applying a pressure between the first and the second chambers to cause the reagent and the blood sample to flow back and forth to affect mixing, thereby obtaining a sample mixture.

The method further comprises withdrawing the sample mixture through the sample outlet into a blood measurement device, through a conduit thereof, in a blood analyzer for one or more measurements of the sample mixture. Moreover, the method further includes withdrawing a cleaning solution contained in a cleaner chamber of the cassette into the blood measurement device to clean the blood measurement device, and returning used sample mixture through the conduit back to the chambers of the cassette through the sample outlet.

In another embodiment, the disposable cassette further comprises a second pair of chambers in a form of depression of the upper panel of the housing and sealed by the diaphragm; portions of the diaphragm over the chambers being flexible; and additional one or more channels adapted to interconnect the second pair of chambers; one of the second pair of chambers containing a predetermined amount of a second reagent for the blood analysis; and a second sample outlet disposed next to and connected to the chamber containing the second reagent. The second sample outlet comprises an outlet cavity recessed from the upper panel and covered by a cover and a divider disposed therein, and the second sample outlet seals the second reagent to the chamber containing the second reagent. Both sample outlets are located on the same side of the pairs of chambers.

In this embodiment, the sampling sled further comprises a second sampling cavity in a form of recess on the flat upper surface. When in the filling position, the second sampling cavity is in fluid communication with the filling inlet, and when in the flushing position, the second sampling cavity is in fluid communication with the channels adapted to interconnect the second pair of chambers.

With this embodiment, the method further comprises isolating a second volume of the blood using the sampling sled; piercing the divider in the second sample outlet by a second piercing element and establishing fluid communication between the first chamber and a second chamber of the second pair of chambers through additional channels; applying a pressure on a portion of the diaphragm over the first chamber of the second pair of chambers, and causing the second reagent to flow through the sampling section, and flushing the second volume of the blood sample into the second chamber of the second pair of chambers; and alternately applying a pressure between the first and the second chambers of the second pair of chambers to cause the second reagent and the second volume of the blood sample to flow back and forth to affect mixing, thereby obtaining a second sample mixture.

The advantages of the present invention will become apparent from the following description taken in conjunction with the accompanying drawings showing exemplary embodiments of the invention.

BRIEF DESCRIPTION OF THE DRAWINGS

FIGS. 4 and 4A are top and bottom perspective views, respectively, of the sampling sled of the disposable cassette shown in FIG. 1. FIG. 4B shows a part of the snap fitting mechanism between the sampling sled and the lower side of the upper panel of the cassette.

FIG. 7A shows the sampling section after a blood sample is filled in. FIG. 7B shows an embodiment in which the cassette has a pair of electrode disposed within vent opening 75 as a blood sensor.

It is noted that in the drawings like numerals refer to like components.

DETAILED DESCRIPTION OF THE INVENTION

In one aspect, the present invention provides a disposable cassette for measurement of blood samples on a blood analyzer, particularly for hematology measurement.

Figure 1:
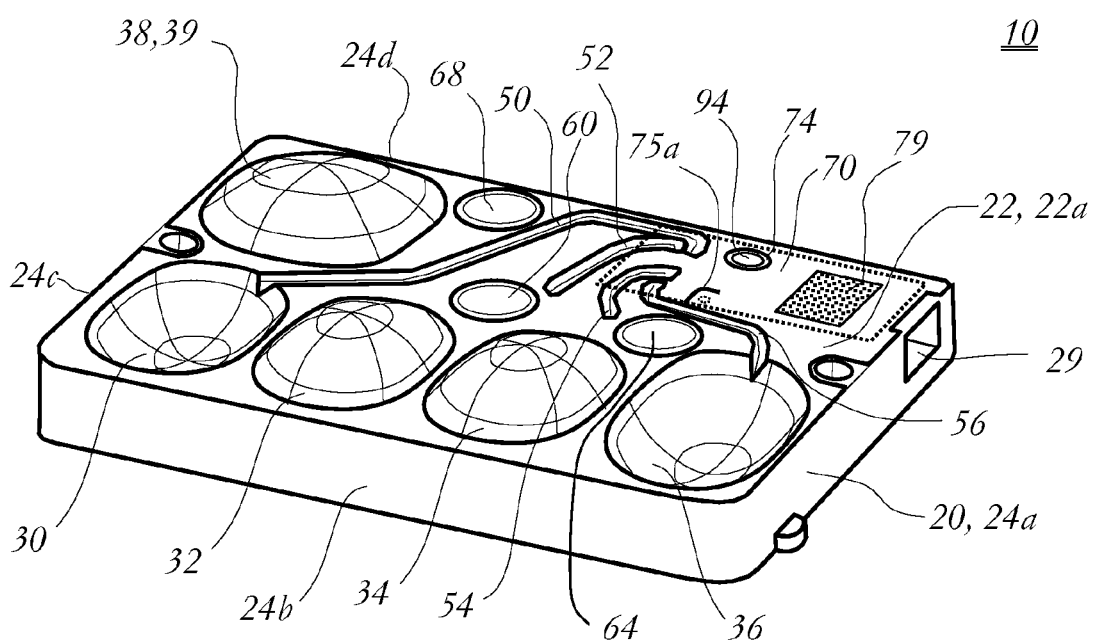
FIG. 1 is a perspective view of the disposable cassette of the present invention.
Figure 2:
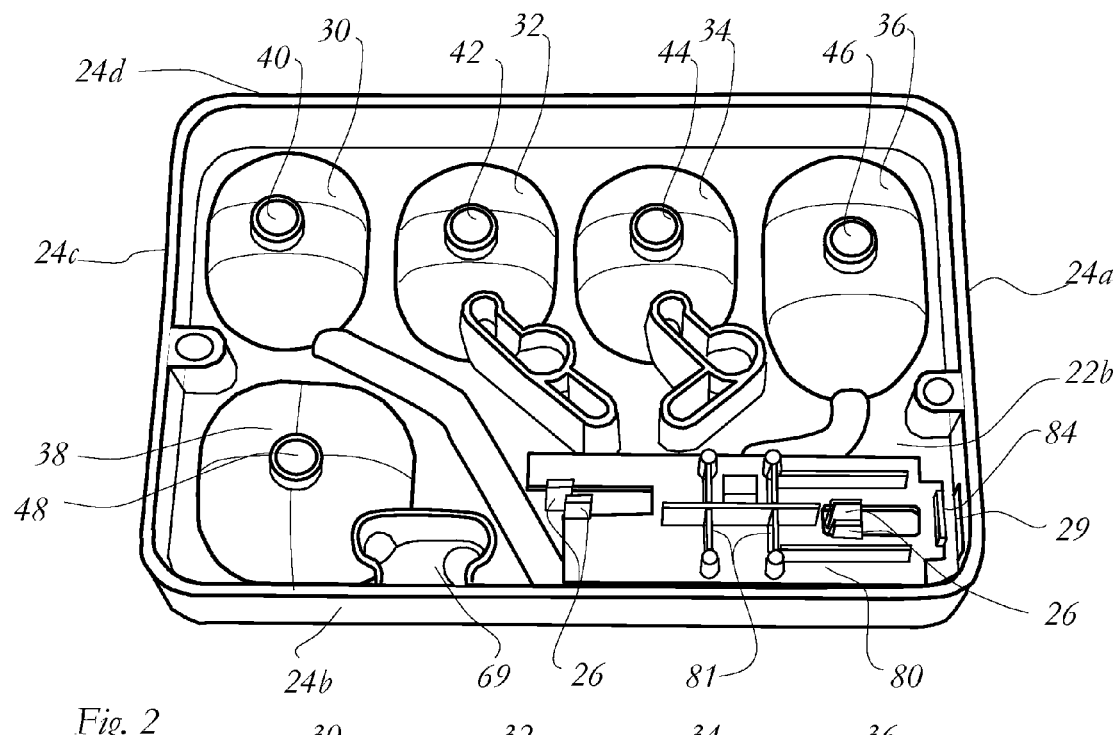
FIG. 2 is a bottom view of the disposable cassette shown in FIG. 1, without the bottom diaphragm.
Figure 3:
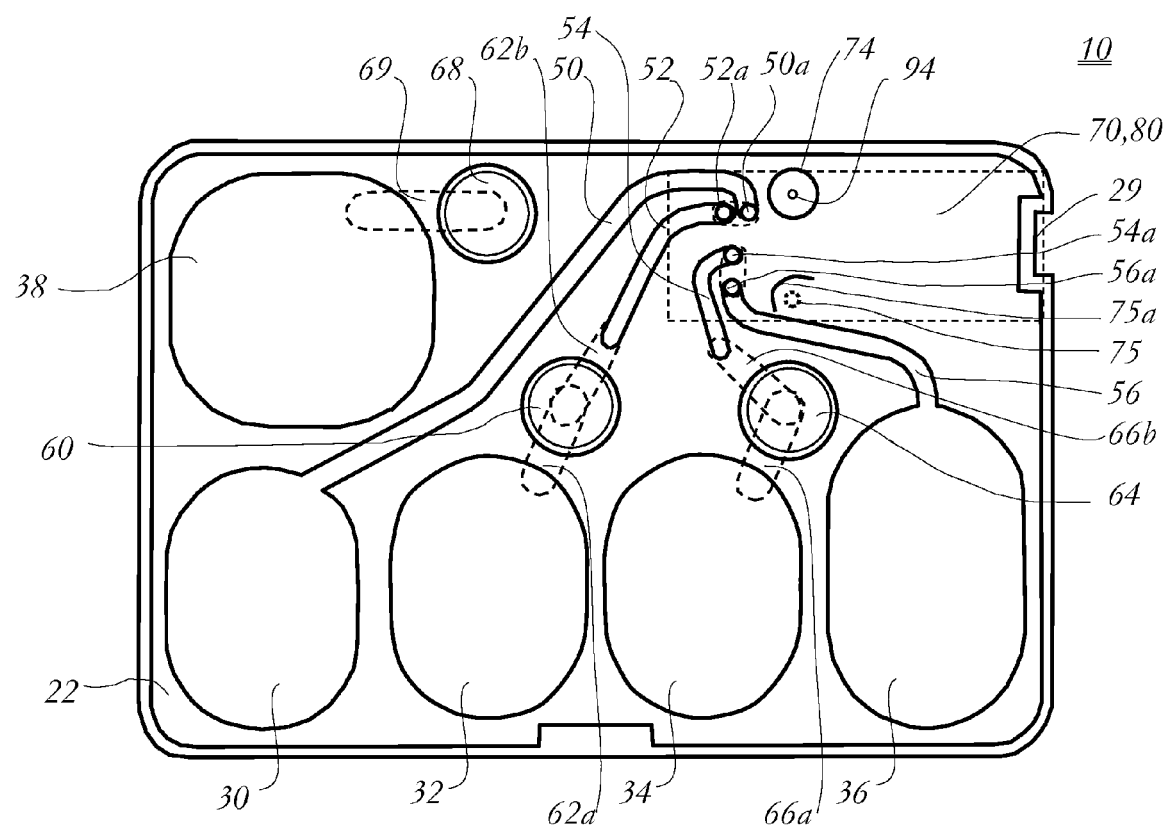
FIG. 3 is a top view of the disposable cassette shown in FIG. 1.

Referring to FIGS. 1-3, in one embodiment, disposable cassette 10 includes a housing 20, which includes an upper panel 22 and side walls 24a-24d. In the embodiment shown, housing 20 has a rectangular block shape with a hollow lower side, having a length about 8 cm, a width about 5 cm, and a height about 1 cm. The disposable cassette includes multiple chambers or receptacles, in a form of depression of upper panel 22 of housing 20 sealed by a diaphragm, and multiple channels adapted to connect selected chambers. As some of these chambers are used for mixing a blood with reagent, they are also referred to as mixing chambers herein. In the embodiment shown, disposable cassette 10 has a first pair of mixing chambers 30 and 32 and a second pair of mixing chambers 34 and 36, and a cleaner chamber 38. All chambers are in a form of depression of upper panel 22 of housing 20 and sealed by a diaphragm 39. In an exemplary embodiment, the mixing chambers have a length about 2.2 cm, a width about 1.6 cm and a depth about 0.8 cm.

Preferably, each chamber has a boarder elevated from upper side 22a of upper panel 22, for example, having a height about 0.5 to 2 mm. When diaphragm 39 is sealed on the upper panel, the diaphragm is heat welded onto the boarders to ensure sealing of the chambers. In the embodiment shown, diaphragm 39 seals the entire upper surface of upper panel 22, which is referred to as the upper side of cassette 10. As can be appreciated, the diaphragm is an integral part of each chamber. Alternatively, each depression can also be sealed by a separate diaphragm. As shown in FIG. 1, diaphragm 39 in the areas above the depressions is in a dome shape, displaced from upper panel 22. The diaphragm is either above upper panel 22 as shown at the positions of chambers 32, 34, and 38 because the chambers are filled with liquid reagents as described below, or substantially rests on the surface of the depressions as shown at the positions of chambers 30 and 36 when the chambers are empty. The diaphragm is flexible in the areas above the depressions.

One chamber in the first pair of mixing chambers, such as chamber 32, is filled with a predetermined volume of a blood diluent. One chamber in the second pair of mixing chambers, such as chamber 34, is filled with a predetermined volume of a lysing reagent. The diluent and lysing reagent are used for preparing a blood sample for measurement on the blood analyzer, which is described further hereinafter. Moreover, cleaner chamber 38 is filled with a cleaning solution.

Both diluent and lysing reagent are reagents used for hematology analysis, which are known in the art. The blood diluent is an isotonic aqueous solution for diluting a blood sample for measuring red blood cells and platelets of a blood sample. The lysing reagent contains a hemolytic agent, typically one or more surfactants, to lyse red blood cells, yet preserves the white blood cells to a certain degree, which allows counting numbers and measuring the size of the white blood cells. The cleaning solution typically contains a surfactant, and may also contain an enzyme.

As shown in FIG. 2, each of the chambers also has a bottom opening at the bottom of the chamber, i.e., openings 40, 42, 44, 46, and 48. In manufacturing cassette 10, diaphragm 39 is sealed on to upper panel 22 first, and then the diluent and lysing reagent are filled into chambers 32 and 34 through opening 42 and 44, and the cleaning solution is filled into chamber 38 through opening 48. After filling, all bottom openings are sealed with another diaphragm. This diaphragm can seal around the bottom edges of side walls 24a to 24d, therefore, it seals the entire lower side of cassette 10. This sealing mechanism has a simple structure, and a low cost in manufacture assembling process. The integral diaphragm structure avoids the use of multiple rubber stoppers typically used in prior art devices, and avoids potential compatibility issue between rubber components and the reagents, particularly during prolonged storage.

Housing 20 is made of a synthetic polymeric material inert to chemicals used in the diluent and lysing reagent and compatible with these reagents and blood. Various suitable materials known in the art can be used for the purpose of the present invention. In one exemplary embodiment, polypropylene is used for plastic molding of the housing. Diaphragm 39 and the second diaphragm used to seal the bottom side of cassette 10 are made of a flexible, thin layer of a synthetic polymeric material, compatible with the reagents and blood. Preferably, the diaphragm is transparent. Various suitable materials known in the art can be used for the purpose of the present invention. In one exemplary embodiment, a laminated polyamide/polypropylene film is used as the diaphragm.

As shown in FIG. 3, cassette 10 includes multiple channels adapted to interconnect mixing chambers, as described in detail below. In the embodiment shown, these channels are formed by grooves on, or depression of, upper panel 22 of housing 20, and the upper side of the grooves are sealed by diaphragm 39 to form channels. With this structure, the grooves can be conveniently manufactured by molding as an integral part of upper panel 22 of housing 20. Preferably, each channel also has a boarder elevated from upper side 22a of upper panel 22, with a similar height of the boarders surrounding the chambers. When diaphragm 39 is sealed on the upper panel, the diaphragm is heat welded onto the boarders of the channels to ensure sealing of the channels.

Figure 2A:
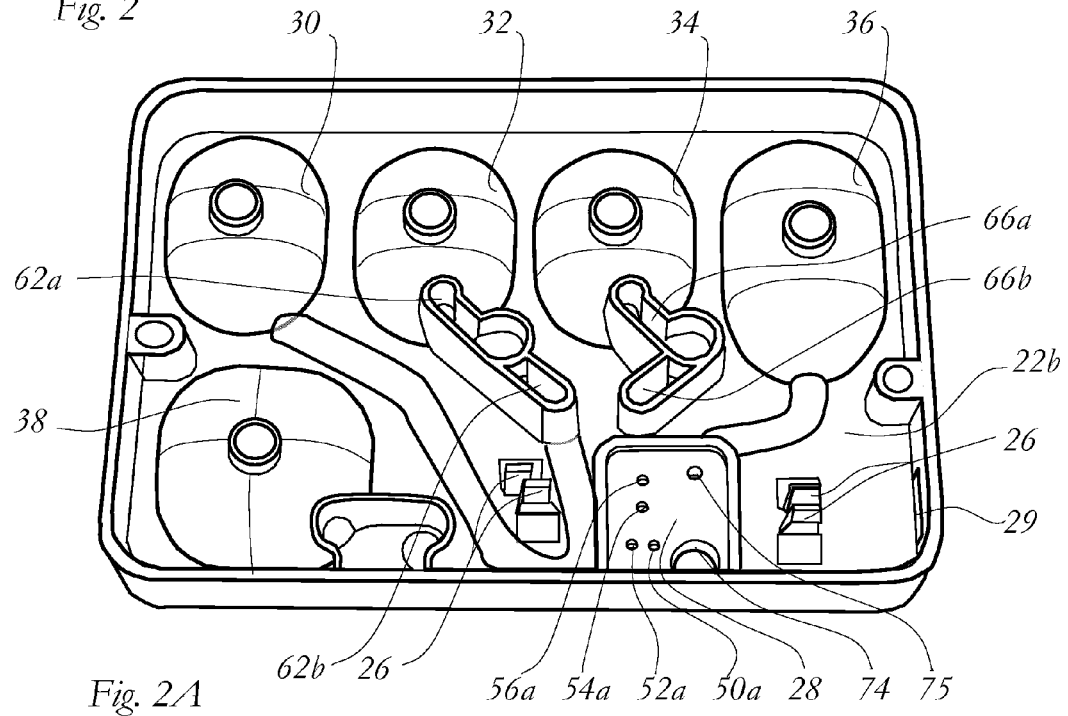
FIG. 2A is a bottom of the disposable cassette, with the sampling sled and the sampling gasket removed from the cassette.
Figure 7:
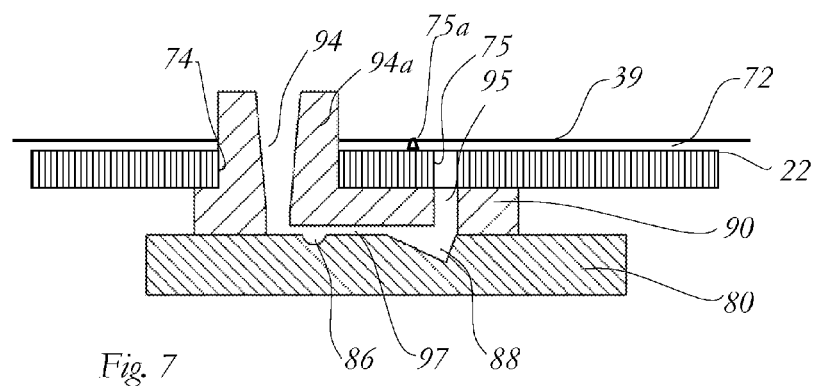
FIG. 7 is an enlarged cross-sectional view of the sampling section of the disposable cassette, along line 2-2' of FIG. 6, showing communications among the filling inlet, the first and second sampling cavities and the venting aperture at the filling position.
Figure 7:
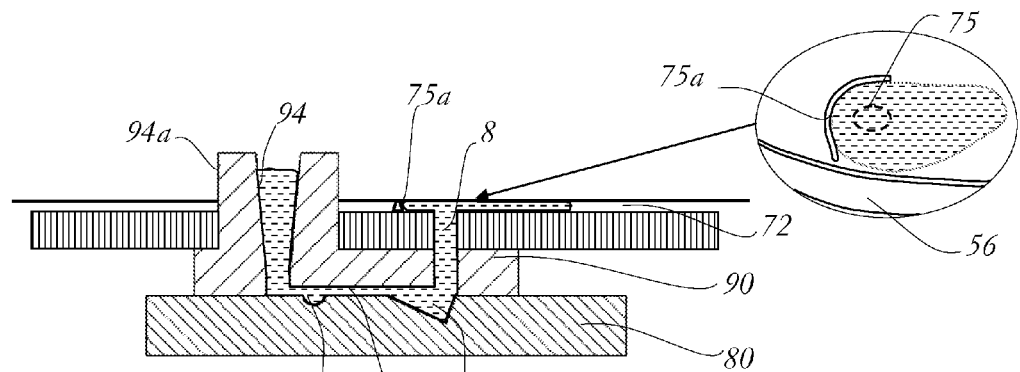
Figure 7:
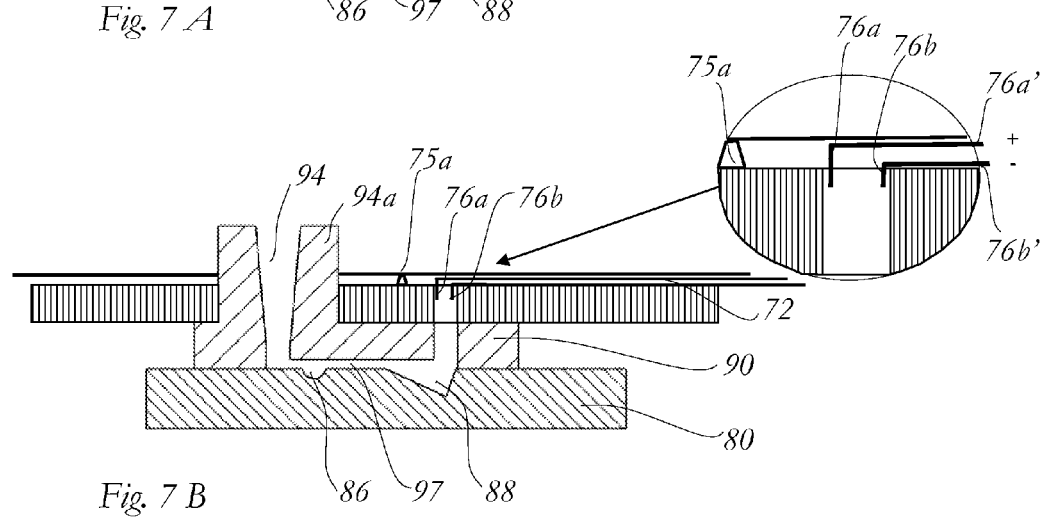

As shown in FIGS. 1 and 3, cassette 10 has a sampling section 70 that has a filling inlet 94 and an externally sealed vent opening 75 (see FIGS. 2A and 3). Upper panel 22 of housing 20 has a filling rim opening 74 (see FIGS. 1 and 2A), within which a filling rim 94a of a sampling gasket 90 is inserted, which is described in detail hereinafter in reference to FIG. 5. As shown in FIGS. 1 and 3, cassette 10 has a vent lip 75a around vent opening 75 elevated from upper side 22a of upper panel 22. In the embodiment shown, lip 75a has a semi-spherical like shape with a height similar to that of the boarders around the chambers. The vent lip can also have other suitable shapes or structures, preferably, it has an open structure, and is not completely closed around the vent opening. When diaphragm 39 seals the entire upper panel 22, the diaphragm is only welded on the boarders surrounding the chambers and the channels, therefore, there is a space between the diaphragm and upper side 22a of upper panel 22 in the rest areas of the upper panel. This space 72 is present in sampling section 70, and vent lip 75a further ensures the distance between the diaphragm and vent opening 75, as shown in FIG. 7. This sealing structure provides an externally sealed venting mechanism to the cassette, and utilities of this unique structural feature are described hereinafter in reference to blood filling. Alternatively, if the diaphragm is welded on the entire upper side of upper panel 22, the area of upper panel 22 around vent opening 75 can be slightly recessed, which provides a space between the diaphragm and the vent opening. Diaphragm 39 leaves an opening over filling rim opening 74, and a blood sample can be filled into the cassette through filling inlet 94 as described hereinafter.

Optionally, cassette 10 may have a pair of electrodes 76a and 76b disposed within vent opening 75 as shown in FIG. 7B, functioning as a blood sensor. The upper ends 76a' and 76b' of the electrodes are located on upper panel 22 or on a side wall of housing 20 forming an electrode interface, which is exposed for electrical contact, with its surroundings sealed by diaphragm 39. The electrode interface is adapted to connect to a detector in a cassette interface of a blood analyzer, when the cassette is used on the blood analyzer.

As shown, the first end of channel 50 connects to mixing chamber 30, and the first end of channel 52 connects to mixing chamber 32 through a sample outlet 60. Similarly, the first end of channel 54 connects to mixing chamber 34 through a sample outlet 64, and the first end of channel 56 connects to mixing chamber 36. The second ends of channels 50 and 52 are positioned next to each other, and the second ends of channels 54 and 56 are positioned next to each other. The second ends of these four channels are disposed in the sampling section 70, adjacent to filling inlet 94. At the second end, each of these four channels has an opening at the bottom of the groove, shown in FIGS. 3 as 50a, 52a, 54a, and 56a, respectively. Channels 50 and 52 are in fluid communication, and channels 54 and 56 are in fluid communication, through a sampling gasket disposed in the sampling section, which will be described in detail hereinafter.

Preferably, disposable cassette 10 further includes a bar code for identifying a specific cassette. In the embodiment shown in FIG. 1, a two-dimensional bar code 79 is used. The bar code can contain desired product information, such as the lot number of diluent or lysing reagent filled in the cassette.

Disposable cassette 10 comprises a sampling sled 80, as shown in FIG. 2, disposed in sampling section 70 of housing 20. FIGS. 4 and 4A show top and bottom perspective views of sampling sled 80, respectively. As shown, sampling sled 80 has a flat upper surface 82, a first sampling cavity 86, and a second sampling cavity 88. Both sampling cavities are in a form of recess on upper surface 82, and each has a predetermined volume. Sampling cavity 86 is used to isolate a predetermined volume of a blood sample for red blood cell measurement. Sampling cavity 88 is used to isolate a predetermined volume of a blood sample for white blood cell measurement. In one exemplary embodiment, sampling cavity 86 has a volume about 0.1 microliter and sampling cavity 88 has a volume about 5 microliter. Because concentration of the red blood cells in a blood sample is substantially higher than concentration of the white blood cells, sampling cavity 86 is substantially smaller than sampling cavity 88.

Sampling sled 80 includes a pusher interface 84, which can be accessed through a pusher window 29 located on side wall 24a (see FIGS. 1 and 2). When cassette 10 is placed into a blood analyzer, a sled pusher 160 (shown in FIGS. 6 and 12) of the blood analyzer pushes on pusher interface 84 to move sampling sled 80 from a filling position to a flushing position, which will be described further hereinafter. Sampling sled 80 further includes a set of enforcement ribs 81 on the back of the sled. Sampling sled 80 is made of a synthetic polymeric material compatible with blood and the reagents used in the cassette. Various suitable materials known in the art can be used for the purpose of the present invention. Preferably, polycarbonate is used for making the sled.

Moreover, sampling sled 80 includes two elongated slots 83 and 85, both are a female portion of a snap fitting mechanism between sampling sled 80 and lower side 22b of upper panel 22 of housing 20. As shown in FIGS. 2 and 2A, sampling section 70 of housing 20 has two pairs of male elements 26 extending from lower side 22b of upper panel 22 for snap fitting of sampling sled 80. As shown in FIG. 4B, once sampling sled 80 is snap fit onto the lower side of upper panel 22, the sled is tightly retained by male elements 26. However, sampling sled 80 is slidable within the length of elongated slot 83, when it is pushed by the pusher.

FIG. 2A shows a bottom perspective view of cassette 10, with sampling sled 80 removed from the cassette. As shown, sampling section 70 of housing 20 has a gasket seat 28, in the form of recess on the lower side of upper panel 22 for seating a sampling gasket 90 described below. Moreover, channel openings 50a, 52a, 54a and 56a of channels 50, 52, 54 and 56, respectively, as well as filling opening 74 and vent opening 75, are located in gasket seat 28.

Figure 5:
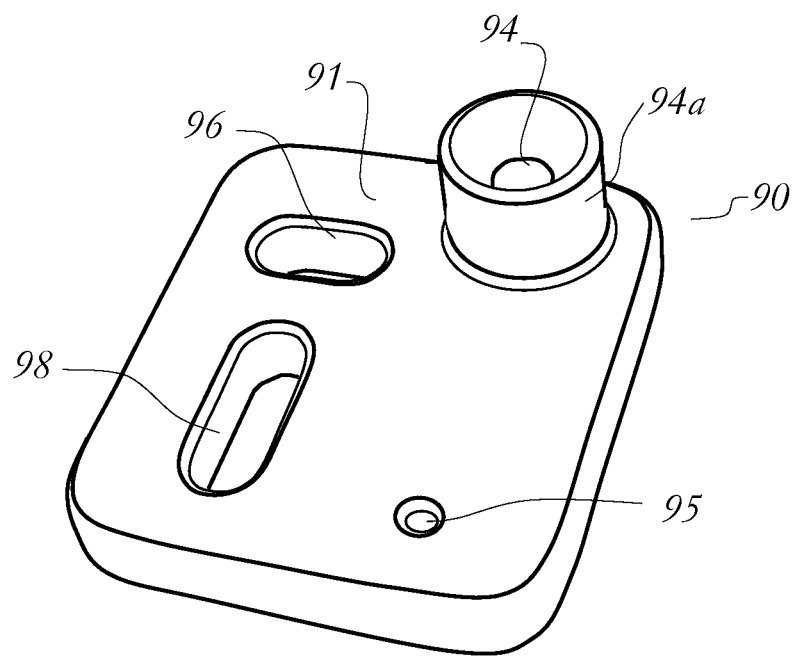
FIGS. 5 and 5A are top and bottom perspective views, respectively, of the sampling gasket of the disposable cassette shown in FIG. 1.
Figure 5A:
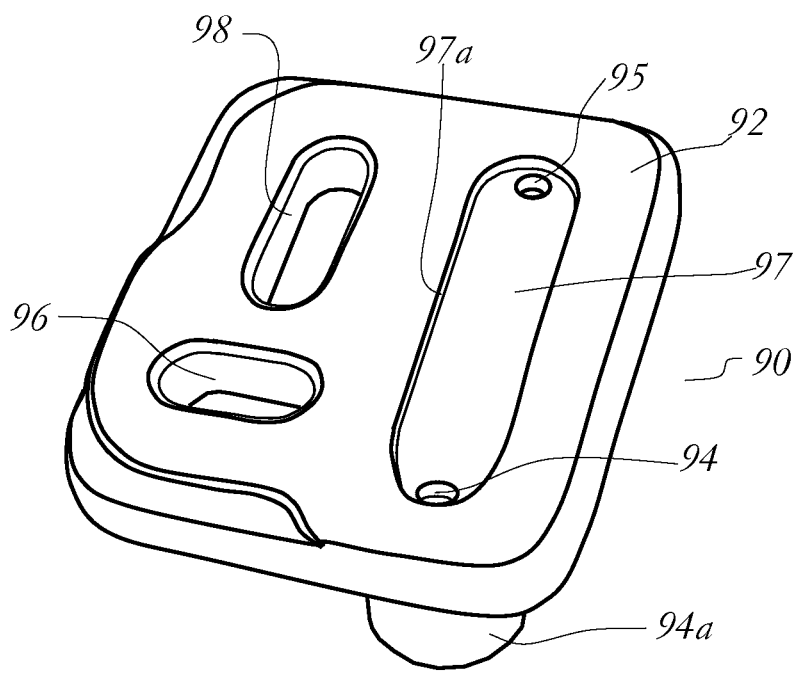

Cassette 10 includes a sampling gasket 90 as shown in FIGS. 5 and 5A, which is disposed within gasket seat 28. Sampling gasket 90 has a flat upper surface 91, which is directly against gasket seat 28 on the lower side of upper panel 22 of housing 20 when sampling gasket 90 is installed. Sampling gasket 90 includes a filling inlet 94 surrounded by a circular filling rim 94a, which has an outer diameter complementary to the inner diameter of filling rim opening 74 of housing 20. Filling rim 94a is inserted into filling rim opening 74, therefore, filling inlet 94 of sampling gasket 90 is directly accessible from the upper side of cassette 10 for filling a blood sample. Sampling gasket 90 also has a venting aperture 95 aligned with vent opening 75 on upper panel 22 of housing 20.

Sampling gasket 90 is made of a resilient material, which is compatible with blood and reagents used in the cassette. Various suitable resilient materials known in the art can be used for the purpose of the present invention. Preferably, silicone is used. The thickness of sampling gasket 90 in dimension is larger than the depth of gasket seat 28, therefore, lower surface 92 of sampling gasket 90 extends out from gasket seat 28, and is directly against flat upper surface 82 of sampling sled 80.

Sampling gasket 90 includes a first through-hole 96, which is positioned below and aligned with channel openings 50a and 52a of channels 50 and 52, and a second through-hole 98, which is positioned below and aligned with channel openings 54a and 56a of channels 54 and 56. As such, channels 50 and 52 are connected by first through-hole 96, thus enabling fluid communication between the first pair of mixing chambers 30 and 32. Similarly, channels 54 and 56 are connected by second through-hole 98, thus enabling fluid communication between the second pair of mixing chambers 34 and 36.

As shown in FIG. 5A, sampling gasket 90 has a flat lower surface 92, which is in direct contact with upper surface 82 of sampling sled 80. On lower surface 92, there is an elongated recess 97 extending from the outer side of filling inlet 94 to the outer side of venting aperture 95. Since the flat lower surface 92 of sampling gasket 90 is against the flat upper surface 82 of sampling sled 80, recess 97 forms a blood filling space.

Figure 6:
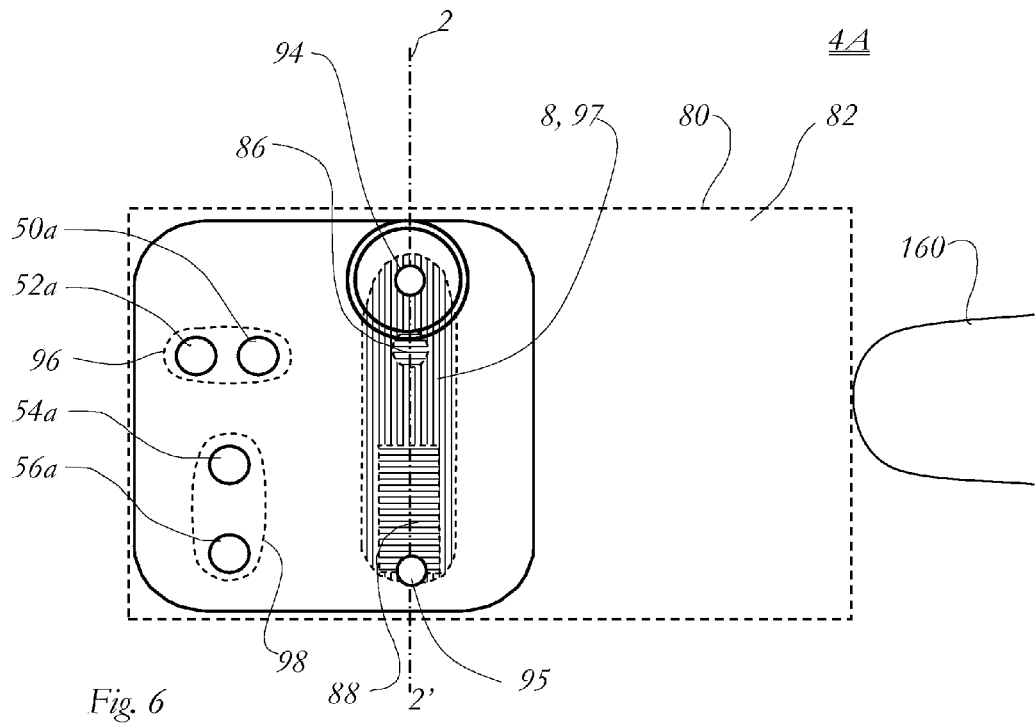
FIGS. 6 and 6A are illustrative views of the sampling section of the disposable cassette, with the sampling sled at the filling position and the flushing position, respectively.
Figure 6A:
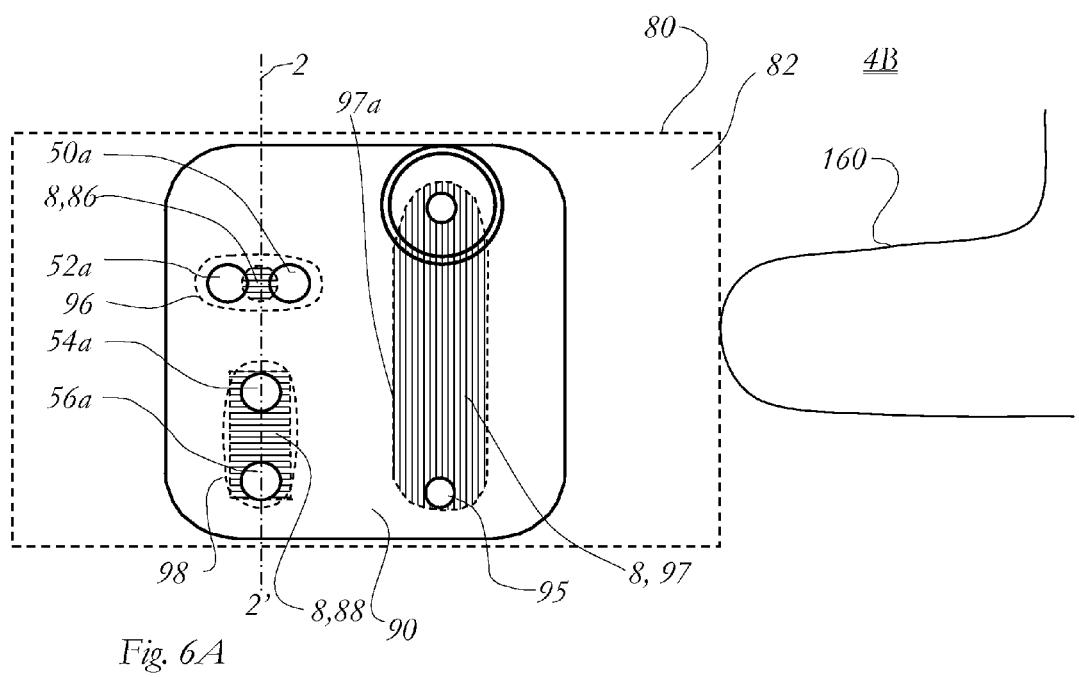

FIGS. 6 and 6A illustrates the sample volume isolation mechanism of the disposable cassette of the present invention. In FIG. 6, sampling sled 80 is at its filling position 4A, and in FIG. 6A, sampling sled 80 is moved into its flushing position 4B, see the relative position of line 2-2' of sampling sled 80. At the filling position 4A, as shown in FIG. 6, filling inlet 94, venting aperture 95, and first and second sampling cavities 86 and 88 of sampling sled 80 are all aligned with line 2-2' of sampling sled 80. As such, when a blood 8 is filled in through filling inlet 94, blood 8 flows into first sampling cavity 86 and the second sampling cavity 88, and fills in recess 97 (see shaded area in FIG. 6).

The communication among filling inlet 94, recess 97, first and second sampling cavities 86 and 88, and venting aperture 95 can be further visualized in FIG. 7, which shows a cross-sectional view along line 2-2' in FIG. 6. During filling, the cassette is at its horizontal position, with filling inlet 94 in an upright position as shown in FIG. 7 (also see FIG. 11). As described previously, vent lip 75a maintains a distance between diaphragm 39 and upper side 72a of upper panel 22 around vent opening 75, and there is a space 72 between the diaphragm 39 and the upper side of upper panel 22. The space may have a height about 1 mm. FIG. 7B illustrates a cross sectional view of the sampling section after a blood sample is filled in. A blood sample can be filled in using a commercially available micropipette, such as 20 μl, or 40 μl micropipette. As shown in FIG. 7B, when 20 μl of a blood 8 is filled in through filling inlet 94, the blood fills in sampling cavities 86 and 88 and recess 97, further into vent opening 75, and with a small amount entering space 72 immediately above vent opening 75. During filling, air within the space of cavities 86 and 88 and recess 97 is released through vent opening 75 into space 72. Therefore, no air bubble presents in the sampling cavities. It should be understood that although diaphragm 39 is sealed over upper panel 22, space 72 is sufficient for releasing air from the space in cavities 86 and 88 and recess 97.

As can be appreciated, the externally sealed venting mechanism of cassette 10 provides sufficient venting of air, yet preventing blood exiting to the exterior of the cassette, therefore, minimizing potential contamination of biohazard material during measurement of a blood sample. Moreover, this externally sealed venting mechanism provides a safe guard against upward blood spill from the vent in the situation of overfill of a sample. As can be further appreciated, in case of serious overfill, space 72 over upper panel 22 functions as a buffer zone to absorb excess amount of blood to prevent potential blood back spill from filling inlet 94.

As can be understood from FIGS. 7A and 7B, in the embodiment shown in FIG. 7B when a blood sample is filled in, electrodes 76a and 76b will immerse in the blood, which closes the circuitry, and the electrical signal generated can be sensed by a detector of the blood analyzer and can be used by the system control for monitoring or controlling the sample preparation process.

Subsequent to filling, sampling sled 80 is pushed into its flushing position 4B as shown in FIG. 6A, by pusher 160, or by an operator's hand. At the flushing position, first and second through-holes 96 and 98 of sampling gasket 90 are aligned with line 2-2' of sampling sled 80. As can be appreciated, when first and second sampling cavities 86 and 88 of sampling sled 80 are moved away from recess 97, the blood above first and second cavities 86 and 88 is sheared off by edge 97a of recess 97 of sampling gasket 90 against the flat upper surface 82 of sampling sled 80. As such, a predetermined volume of the blood is segmented or isolated in first sampling cavity 86 for red blood cell measurement and a predetermined volume of the blood is segmented or isolated in second sampling cavity 88 for white blood cell measurement, respectively.

Using the sample isolation mechanism of the disposable cassette of the present invention, a very small volume of blood is needed for measurements of a blood sample for reporting a complete blood count (CBC, with 16 Hematology parameters). Typically, only about 20 μl of a blood is filled into the cassette using a micropipette. Furthermore, since the filling volume is not directly related to the isolated sample volume for measurement, the requirement on filling volume of a blood sample is more tolerant. Typically, the cassette has an about 20% error range in filling volume, therefore, minimum training and skill level are required for the operator. Moreover, a blood sample can be directly filled in using a commercially available micropipette, without using a tissue to wipe out the blood remained on the outside of the pipette to avoid error caused by the excess amount of blood. As such, potential particle contaminations resulted from using the tissue are prevented.

As can be further appreciated from FIG. 6A, at flushing position 4B, channel openings 50a and 52a are connected with first sampling cavity 86 by first through-hole 96 of sampling gasket 90, and channel openings 54a and 56a are connected with second sampling cavity 88 by second through-hole 98 of sampling gasket 90, respectively. As such, chambers 30 and 32 are in fluid communication through channels 50 and 52, and chambers 34 and 36 are in fluid communication through channels 54 and 56. At this position, the blood diluent in mixing chamber 32 flows from channel 52 through first sampling cavity 86 into channel 50, which carries the predetermined volume of the blood in first sampling cavity 86 into mixing chamber 30. Similarly, the lysing reagent in mixing chamber 54 flows from channel 34 through second sampling cavity 88 into channel 56, which carries the predetermined volume of the blood in second sampling cavity 88 into mixing chamber 36.

Figure 8:
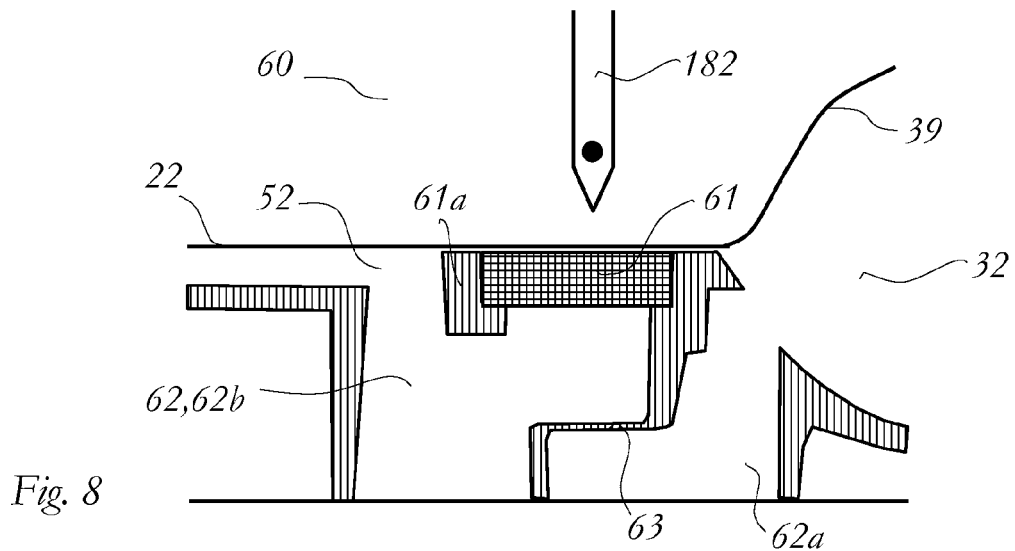
FIGS. 8-8B are illustrative cross-sectional views of the first sample outlet, showing the two segment structure and interaction of a piercing needle with the sample outlet.
Figure 8A:
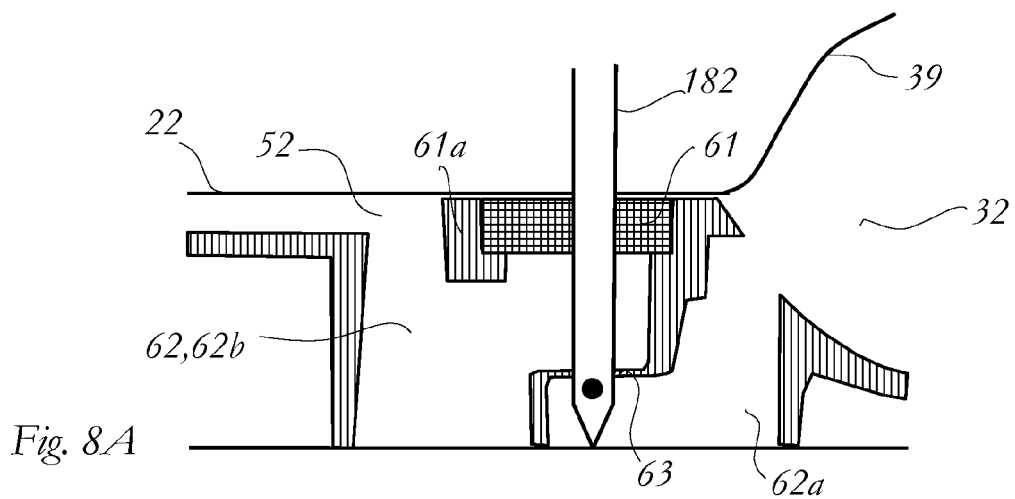
Figure 8B:
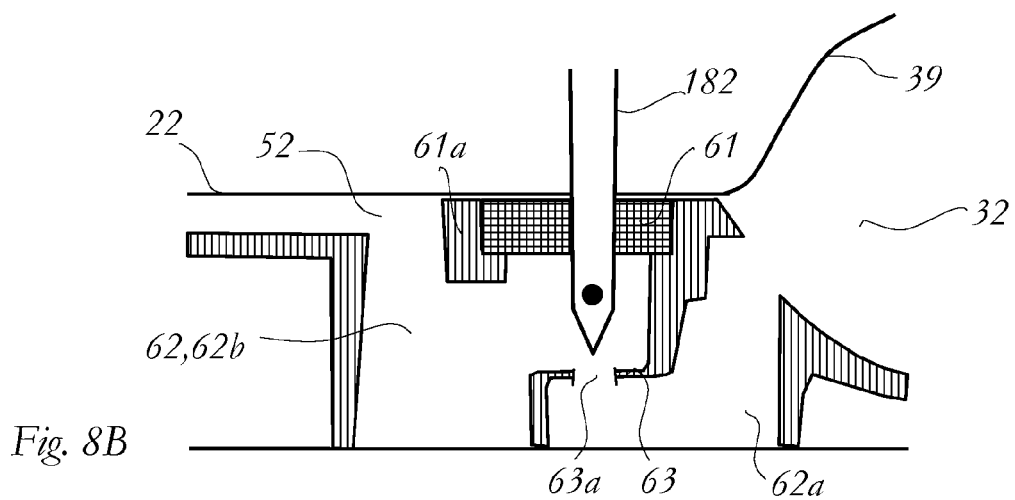

Now, referring to FIGS. 1, 3, and 8-8B, disposable cassette 10 further includes first sample outlet 60, second sample outlet 64, and cleaner outlet 68, through which the sample mixtures and the cleaning solution are released into the conduits of the blood analyzer. FIGS. 8-8B show detailed structure of sample outlet 60 and the working mechanism of the sample outlet. As shown, first sample outlet 60 includes an outlet cavity 62, which is recessed from upper panel 22 of housing 20, and a cover 61. The outlet cavity 62 comprises segment 62a and segment 62b, which are separated by a divider, or membrane 63. As shown, segment 62a is positioned next to and connected to mixing chamber 32, and segment 62b is connected to channel 52 (also see FIGS. 3 and 2A). Before cassette 10 is engaged with the blood analyzer, the blood diluent pre-filled in mixing chamber 32 is retained in chamber 32 and segment 62a of first sample outlet 60, and is sealed by membrane 63, which blocks the diluent from flowing into other parts of the cassette. As illustrated in FIGS. 8A and 8B, when cassette 10 is engaged with the blood analyzer for measuring a blood sample, a piercing needle 182 pierces cover 61, penetrates membrane 63, and creates an opening 63a. When piercing needle 182 retrieves slightly (as shown in FIG. 8B), segments 62a and 62b are in fluid communication through opening 63a, which in turn enables fluid communication between the first pair of mixing chambers 30 and 32. After mixing, which will be further described hereinafter, the first sample mixture, formed between the first volume of the blood isolated by first sampling cavity 86 and the blood diluent, is withdrawn from first sample outlet 60 through needle 182 into a conduit of the blood analyzer for measurement.

The structure of second sample outlet 64 is substantially similar to that of first sample outlet 60, having an outlet cavity with two segments 66a and 66b as shown in FIG. 3, separated by a divider or membrane (not shown). Segment 66a is connected to mixing chamber 34, and segment 66b is connected to channel 54. The operation mechanism of second sample outlet 64 is the same as that described above in first sample outlet 60.

Figure 12:
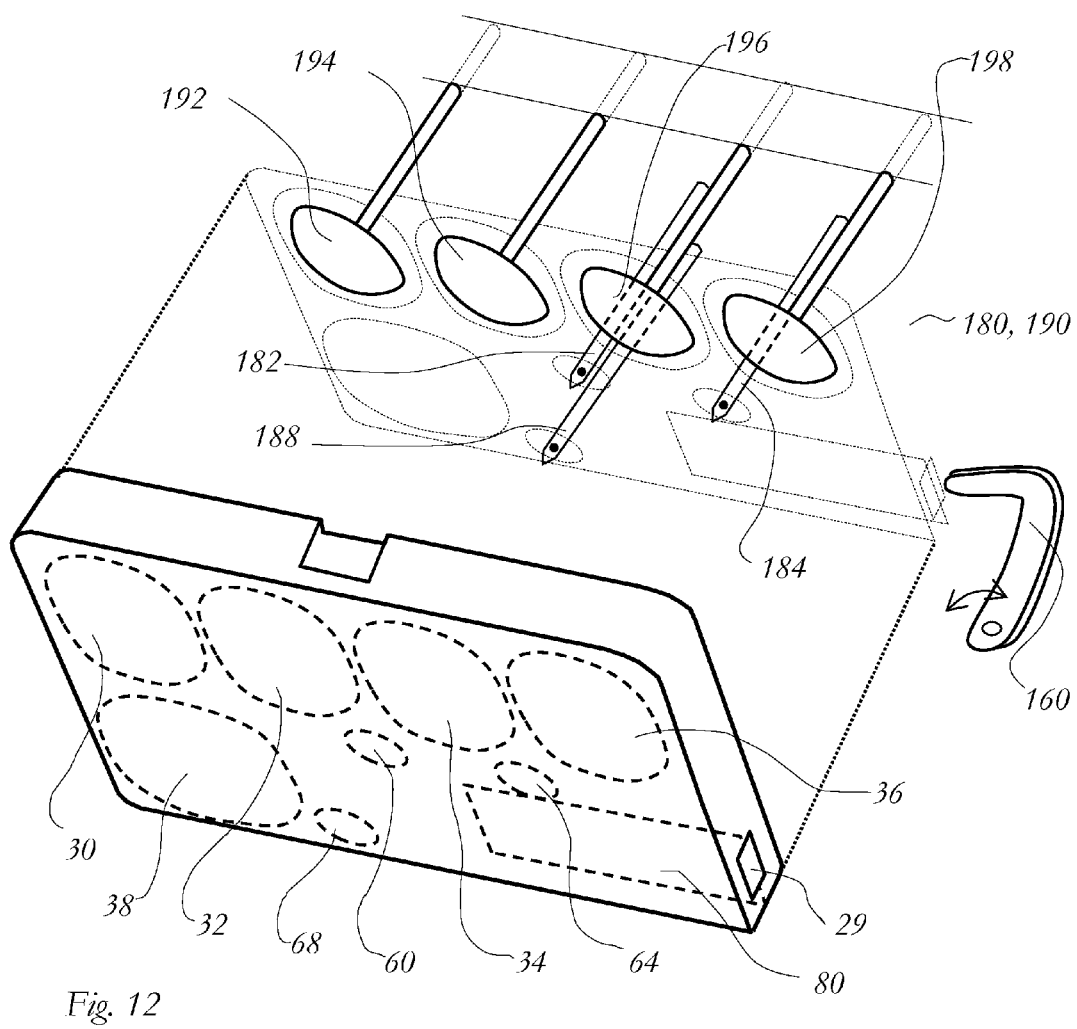
FIG. 12 is an illustrative view showing the engagement of the disposable cassette with the piercing elements of the cassette interface of the blood measurement assembly of the blood analyzer.

Both sample outlets 60 and 64 are positioned on one side of the mixing chambers, i.e., between the sampling section and the mixing chambers. During sample preparation process on a blood analyzer, cassette 10 is in its vertical position and both sample outlets 60 and 64 are below the mixing chambers, as shown in FIG. 12. This structural arrangement minimizes the possibility of air bubbles in the sample outlets, which is further described later.

The divider can be a thin layer, for example 0.2 to 03 mm thickness, of the same polymeric material used in making the housing, and can be made as an integral part of the housing by plastic molding. However, the divider can also be a separate component, such as a separate membrane piece, a welded door, disposed between the two segments. Moreover, other suitable alternative divisions between the two segments can also be used for the purpose of the present invention. For example, in one alternative, the divider is positioned next to the pierceable cover, instead of underneath as shown in FIG. 8. A pin is disposed above the divider, which can be pushed in to break the divider. Another alternative is to use a two-hole needle. In this design, when the needle penetrated the membrane, the lower hole is immersed into the reagent sealed within segment 62a, and the upper hole stays above the membrane in segment 62b, and then the needle itself becomes a conduit communicating between the two segments.

As shown in FIG. 8, cover 61 is seated in a cover seat 61a, which is recessed from upper panel 22 of the housing. As such, cover 61 is completely surrounded and supported by seat 61a around its periphery, which provides a secure sealing around cover 61 to prevent leaking. The cover of the sample outlets is made of a resilient material, therefore, it provides secure sealing around the piecing needle. The resilient material is compatible with reagents used in the cassette and blood. Various suitable resilient materials known in the art can be used for the purpose of the present invention. Preferably, silicone is used.

As can be appreciated, the sample outlets have multiple functions. On one hand, the first or the second sample outlet seals one reagent to only one chamber, and restricts the reagents from flowing into the sampling section and other chamber and channels of the cassette. This restriction prior to use substantially reduces the risk of leaking during storage and transportation of the cassette. On the other hand, once the divider is pierced, each sample outlet becomes a part of the channels, interconnecting two mixing chambers within a pair. Moreover, the sample outlets are also the ports from which the prepared sample mixtures are withdrawn from the cassette into the blood analyzer for measurements; and after the measurements the used sample mixtures are also delivered back to the cassette through the sample outlets, as further described hereinafter.

Cleaner outlet 68 has a simpler structure, which has an outlet cavity 69 covered by a cover made of a resilient material as described above. The outlet cavity 69 is a recess from upper panel 22 of housing 20, and extends on one side, connecting to cleaner chamber 38 (see FIGS. 2 and 3). The cleaning solution filled in cleaner chamber 38 can be withdrawn from cleaner outlet 68, using a piercing element such as a needle, in a similar manner shown in FIG. 8B.

Preferably, each of the outlets described above also has a boarder elevated from upper side 22a of upper panel 22, with a similar height of the boarders surrounding the chambers and channels. When diaphragm 39 is sealed on the upper panel, the diaphragm is heat welded onto the boarders of the outlets to seal the outlets. When the covers of the outlets are pierced as described above, diaphragm 39 above the covers is also pierced.

Figure 9:
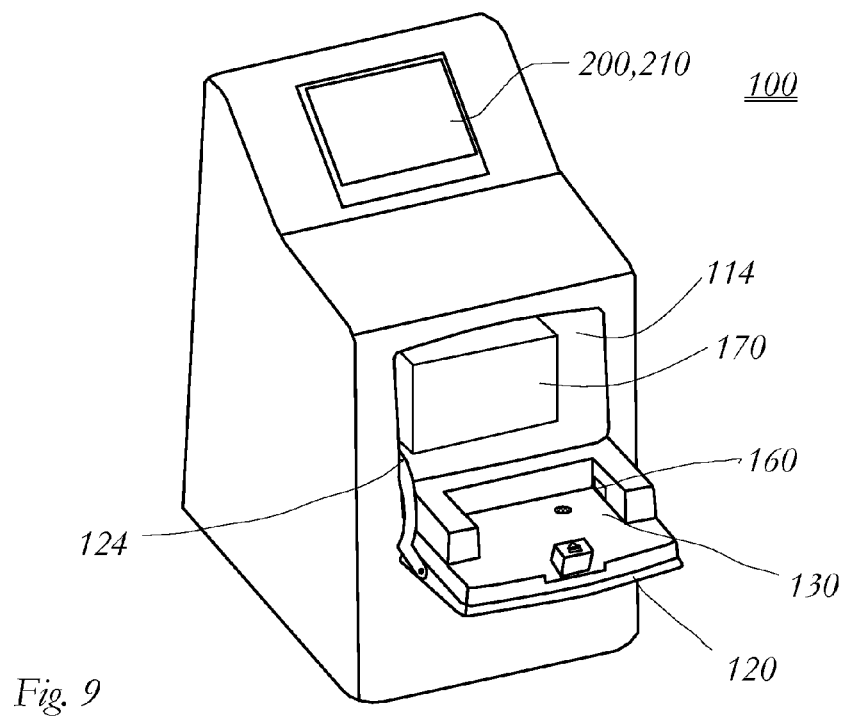
FIG. 9 is a perspective view of the blood analyzer in one embodiment of the present invention, on which the disposable cassette is used, wherein the cassette receiving interface, in a form of movable door, is in an open position.
Figure 9A:
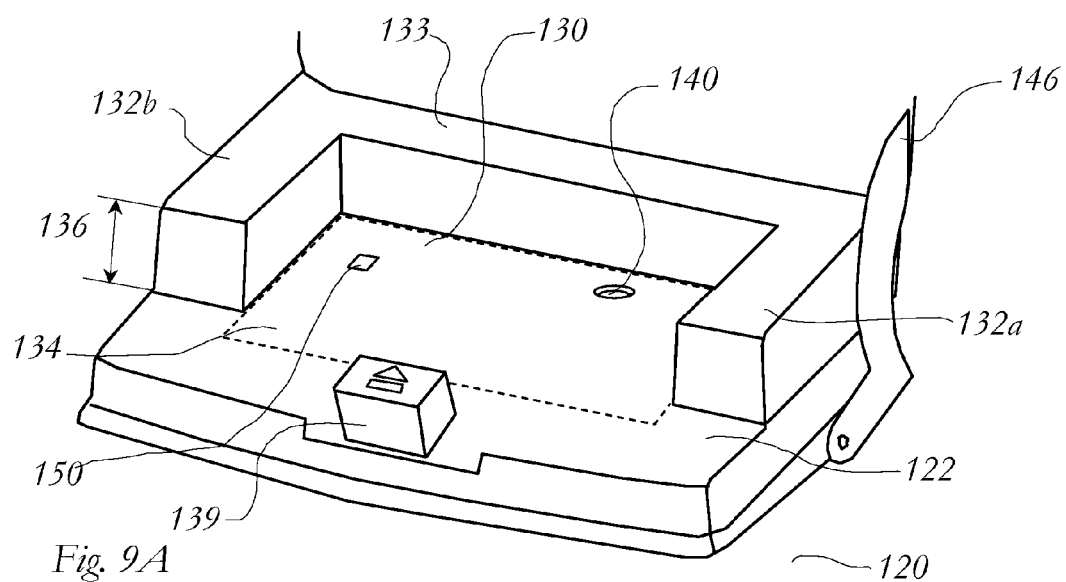
FIG. 9A is a front perspective view of the cassette receiving interface of the blood analyzer shown in FIG. 9 in a horizontal, open position.
Figure 13:
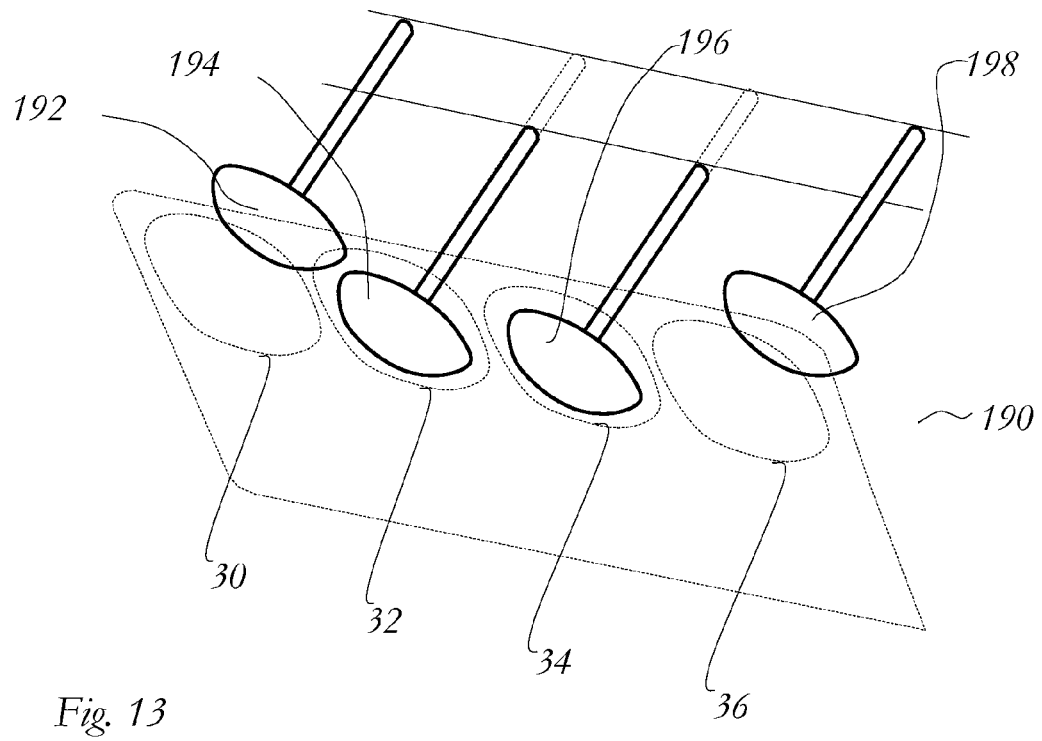
FIGS. 13 and 13A are illustrative views showing alternate movements of plungers of the pressure mixing assembly of the blood analyzer, applying pressures on selected mixing chambers.

Disposable cassette 10 is used on a blood analyzer, which is described hereinafter. Referring now to FIGS. 9, 9A, and 13, blood analyzer 100 includes a cassette receiving interface 120, a blood measurement assembly 170, a pressure actuator assembly 190, a system control 200, and a user interface 210.

In the embodiment shown in FIGS. 9 and 9A, cassette receiving interface 120 is in a form of a door, and movable between a closed position and an open position using door hinges 124. FIG. 9A shows cassette receiving interface 120 in an open, horizontal position. Cassette receiving interface 120 comprises a door panel 122 and a cassette compartment 130, which is formed by two side walls, 132a and 132b, a rear wall 133 and a front stopper 139 on a substantially planar base 134. In the embodiment shown, base 134 is the interior surface of door panel 122; however, the cassette compartment can also be a separate unit from the door panel. Cassette compartment 130 has a width between the two side walls complimentary to the width of disposable cassette 10. Preferably, the height 136 of the walls in dimension is larger than the thickness of the cassette. With the structure and dimensions of cassette compartment 130, disposable cassette 10 is firmly held within the compartment during sample preparation process carried out by the blood analyzer.

Figure 10:
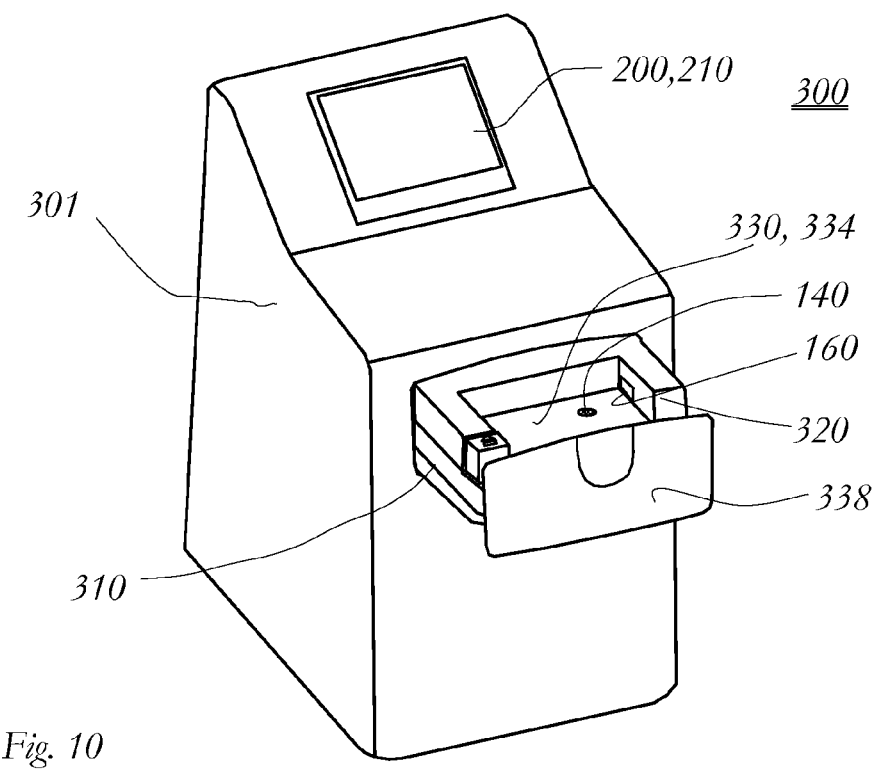
FIG. 10 is a perspective view of the blood analyzer in another embodiment of the present invention, on which the disposable cassette is used, wherein the cassette receiving interface, in a form of a movable tray, is in an open position.

FIG. 10 shows an alternative embodiment of the blood analyzer, on which the disposable cassette of the present invention can be used. As shown, blood analyzer 300 includes a cassette receiving interface 320 in a form of sliding tray. Cassette receiving interface 320 has a front panel 338, support 310 having a sliding mechanism underneath (not shown) similar to that used for opening and closing a compact disk driver. There is a cassette compartment 330 disposed above support panel 310. The structure of cassette compartment 330 is similar to cassette compartment 130 of blood analyzer 100, with a base 334 and sidewalls, and dimensions of cassette compartment 330 is substantially the same as those of cassette compartment 130. When cassette receiving interface 320 is in its open position as shown in FIG. 10, disposable cassette 10 can be placed inside cassette compartment 330. When cassette receiving interface 320 is closed by sliding into system housing 301 of the blood analyzer 300, cassette compartment 330 rotates to a vertical position by a rotation mechanism (not shown), which brings cassette 10 to the same orientation as it is in blood analyzer 100 when cassette receiving interface 120 is at its closed position. In this embodiment, the blood measurement assembly, pressure actuator assembly, system control, and user interface are the same as those of blood analyzer 100, which are described in further detail hereinafter.

Optionally, cassette receiving interface 120 or 320 further comprises a blood sensor 140 operable to detect the presence of blood in disposable cassette 10, when the cassette is placed within cassette compartment 130, or 330, during the measurement of a blood sample. In one embodiment, the blood sensor is an optical sensor, which is known in the art. Moreover, cassette receiving interface 120, or 320, may also include a cassette sensor 150, on base 134 or other locations of cassette compartment 130, which is operable to detect the presence of disposable cassette 10 in the cassette compartment. Cassette sensor 150 can be a mechanical, electrical or optical sensor. Both blood and cassette sensors are connected to the system control and the information provided by the sensors can be used by the system control for controlling automated sample preparation and measurement. For example, when the cassette sensor indicates absence of a cassette in the cassette compartment, or the blood sensor indicates absence of blood in the cassette, the blood analyzer will not initiate the sample preparation process which is described herein later.

Moreover, blood analyzer 100 or 300, further comprises a position sensor operable to detect the position of cassette receiving interface 120 or 320. The position sensor can be a mechanical, electrical or optical sensor, positioned at a suitable location of cassette receiving interface 120 or 320, or at other suitable locations of the blood analyzer. In the embodiment shown in FIGS. 9 and 9A, position sensor 146 of blood analyzer 100, which is an electrical micro-switch, is located at the end of door hinge 124. Position sensor 146 detects cassette receiving interface 120 in its closed or open position, or horizontal or vertical position. The position sensor is electrically connected to the system control, and the signal indicating an open or closed position of cassette receiving interface can be used by the system control in controlling operation of the blood analyzer described further hereinafter.

Blood measurement assembly 170 comprises one or more blood measurement devices operable to measure blood cells and/or contents thereof in a blood sample. In one embodiment, blood measurement assembly 170 comprises two blood measurement devices, one of which is used for measuring red blood cells and platelets of a blood sample and the other is used for measuring white blood cells of the blood sample. The blood measurement device comprises a flow path having an aperture, and a detector disposed adjacent to the aperture to detect individual cells passing through the aperture. The detector can be either an electrical detector or an optical detector. The electrical detector measures direct current impedance signals (DC), or radio frequency impedance signals (RF), generated when each blood cell suspended in an aqueous conductive sample mixture passes through the aperture. The impedance signals are used for counting number of cells and determining size of the cells in the sample mixture. The optical detector measures light scatter or absorption signals generated by blood cells passing through the aperture and these signals are used for counting number of cells and determining size of the cells in the sample mixture. Suitable electrical detectors and optical detectors known in the art for measuring blood cells can be used for the purpose of the present invention.

Blood measurement assembly 170 further comprises a hemoglobin measurement device, which comprises a cuvette with a light path of a determined length, a light source, and an optical detector in alignment with the light path to measure absorption of light passing through the cuvette. Preferably, the cuvette is fluidly connected with the blood measurement device that is used for measuring white blood cells, as such hemoglobin concentration and the white blood cells of a blood sample can be measured using one sample mixture. In measuring white blood cells and hemoglobin concentration, a volume of a blood sample is mixed with a lysing reagent to lyse red blood cells and release hemoglobin molecules, which form a hemoglobin chromogen, typically with a hemoglobin ligand or stabilizer contained in the lysing reagent. The formed sample mixture is passed through the aperture of the flow path, as well as the cuvette, and the white blood cells and hemoglobin concentration can be measured sequentially using the same sample mixture.

Alternatively, two separate sample mixtures can be prepared and used for measuring the white blood cells and hemoglobin concentration. In this arrangement, the hemoglobin measurement device is separated from the flow path that is used for measuring white blood cells.

The signals generated in measuring red blood cells, white blood cells and hemoglobin concentration are processed by a data processor, which can be either independent, or integrated into system control 200.

Blood measurement assembly 170 further comprises a cassette interface 180 that is adapted to fluidly connect with disposable cassette 10, and cause delivery of a prepared sample mixture in disposable cassette 10 into blood measurement assembly 170 for measurement, as well as to cause delivery of the cleaning solution into blood measurement assembly 170 for cleaning the blood measurement devices after the measurements.

In one embodiment, cassette interface 180 comprises one or more piercing elements, such as needles 182, 184, and 188 as shown in FIG. 12, operable to engage with first and second sample outlets 60 and 64, and cleaner outlet 68 of disposable cassette 10 by piercing. Each needle is connected to a conduit (not shown) that is connected to one or more flow path of the blood measurement devices. Operation of cassette interface 180 is described further hereinafter.

Blood analyzer 100 further comprises a pressure actuator assembly 190, which is operable to apply a pressure on selected mixing chambers of disposable cassette 10 for mixing a predetermined volume of a blood with the blood diluent or the lysing reagent. In one embodiment, pressure mixing assembly 190 comprises multiple plungers, 192, 194, 196, and 198 as schematically shown in FIG. 12. Each plunger is adapted to apply a pressure on an area of diaphragm 39 above one mixing chamber of disposable cassette 10, when the cassette is placed within cassette receiving interface 120 or 320 of blood analyzer 100 or 300. In the embodiment shown in FIG. 12, the plungers are in a form of a mushroom, each having a semi-spherical plunger head and a stem. The plungers are driven by one or more motor (not shown). In the embodiment shown, each plunger applies a pressure on a selected mixing chamber of disposable cassette 10 by a linear movement in a direction toward the mixing chamber. FIG. 12 illustrates a phantom plane of disposable cassette 10, schematically showing engagement of plungers 192, 194, 196, and 198 with mixing chambers 130, 132, 134, and 136, respectively (for clarity, the corresponding numbers for the chambers and the outlets are indicated only on the cassette, not on the phantom plane). FIG. 12 further illustrates engagement of needles 182, 184, and 188 with sample outlets 60 and 64, and cleaner outlets 68, respectively. Alternatively, the plungers can also be in a form of cam, which applies pressure on selected mixing chambers by a rotational movement.

The process of using the disposable cassette of the present invention for preparing and measuring a blood sample is described now using blood analyzer 100 as an example in reference to drawings, particularly FIGS. 11, 12, 13-13A, and 14-14A.

Figure 11:
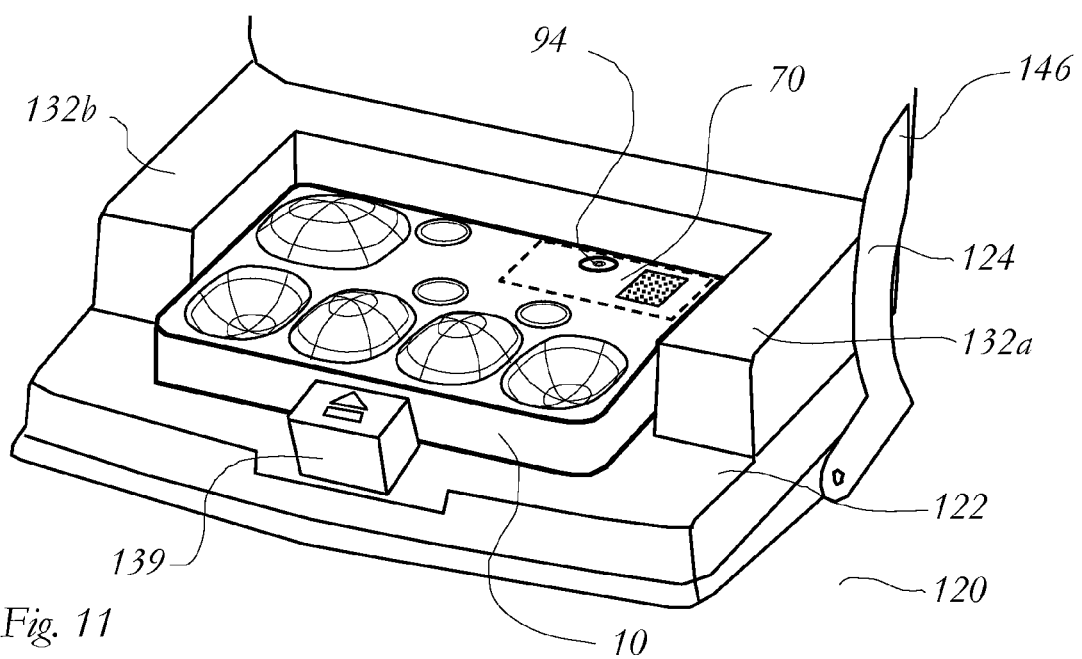
FIG. 11 is a front perspective view of the cassette receiving interface of the blood analyzer shown in FIG. 9 in a horizontal, open position, having a disposable cassette placed within the cassette compartment.

In the process of measuring a blood sample on the blood analyzer, a disposable cassette 10 is placed into cassette compartment 130 of cassette receiving interface 120 at its open position as shown in FIG. 11. As shown, upper side of cassette 10 faces up, with sampling section 70 toward inside of the blood analyzer. At this position, an operator fills a blood sample using a micropipette through filling inlet 94 into the cassette, and moves cassette receiving interface 120 to the closed position after filling. Once cassette receiving interface 120 is in the closed position, as can be indicated by the position sensor, the blood analyzer activates cassette interface 180 of blood measurement assembly 170 to move needles 182, 184, and 188 forward the cassette and to penetrate into first and second sample outlets 60 and 64, and cleaner outlet 68, respectively, as shown in FIG. 12. It is noted in FIG. 12 the upper side of cassette 10 faces the inside of the blood analyzer, with the lower side of cassette 10 against the door panel. As described above, needle 182 is moved to penetrate membrane 63 in outlet cavity 62, and then is retrieved slightly, which enables the fluid communication between mixing chamber 32 and channel 52 through the opening 63a on membrane 63. The same is also accomplished by needle 184 in second sample outlet 64. In the case of cleaner outlet 68, needle 188 simply penetrates the cover into the cleaning solution filled therein. At this point, the blood analyzer activates pressure actuator assembly 190 to apply a pressure on selected mixing chambers.

Figure 14:
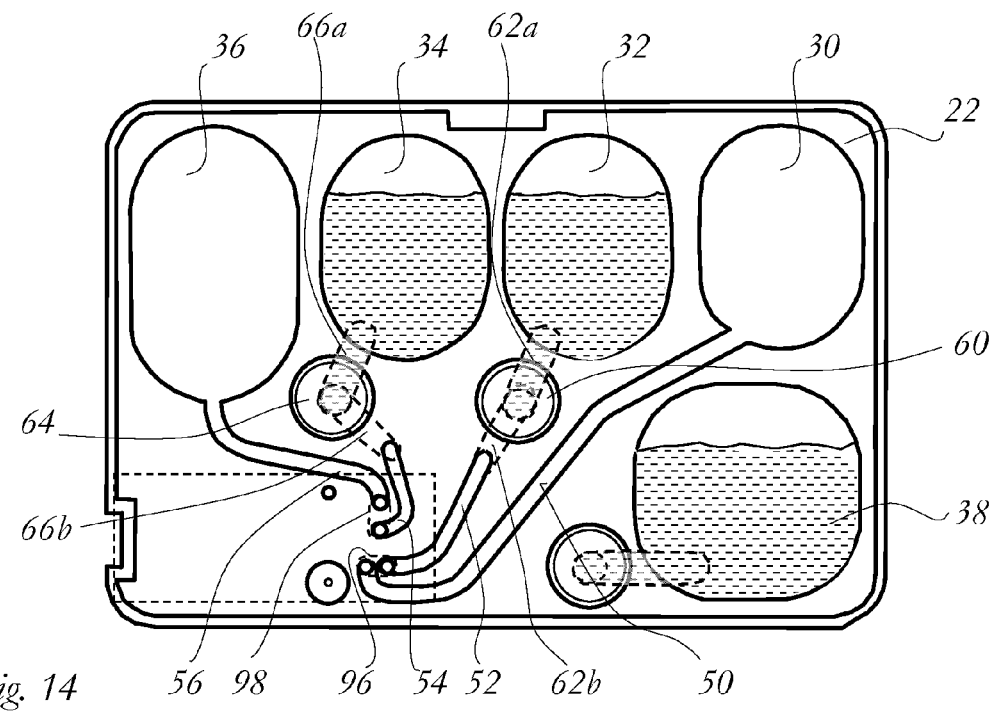
FIGS. 14 and 14A are illustrative views of the disposable cassette showing movements of the first sample mixture within the first pair of mixing chambers and the second sample mixture within the second pair of mixing chambers during the process of preparing a blood sample for red blood cell and white blood cell measurements on the blood analyzer.

As shown in FIG. 12, at the closed position of cassette receiving interface 120, plungers 192, 194, 196, and 198 are immediately adjacent to mixing chambers 30, 32, 34, and 36, respectively. Pressure actuator assembly 190 first moves plungers 194 and 196 forward and apply a pressure on diaphragm 39 at the areas above mixing chamber 32 and mixing chamber 34, as illustrated in FIG. 13. As described above, mixing chamber 32 is filled with a diluent and mixing chamber 34 is filled with a lysing reagent, which is schematically shown in FIG. 14. It is noted that in FIGS. 14 and 14A cassette 10 is viewed in a direction from the inside of the blood analyzer toward the door panel of the blood analyzer. Considering the first pair of mixing chambers 30 and 32, when a pressure is applied by plunger 194 on mixing chamber 32, the diluent flows out from mixing chamber 32 through segments 62a and 62b of first sample outlet 60 into channel 52, then through through-hole 96 into channel 50, and then into mixing chamber 30. Similarly, when a pressure is applied by plunger 196 on mixing chamber 34, the lysing reagent flows out from mixing chamber 34 through segments 66a and 66b of second sample outlet 64 into channel 54, then through through-hole 98 into channel 56, and then into mixing chamber 36. As such, the channels, through-hole, and mixing chambers within each pair are primed with the respective reagent contained therein, and all contact surface areas are wet.

Figure 14A:
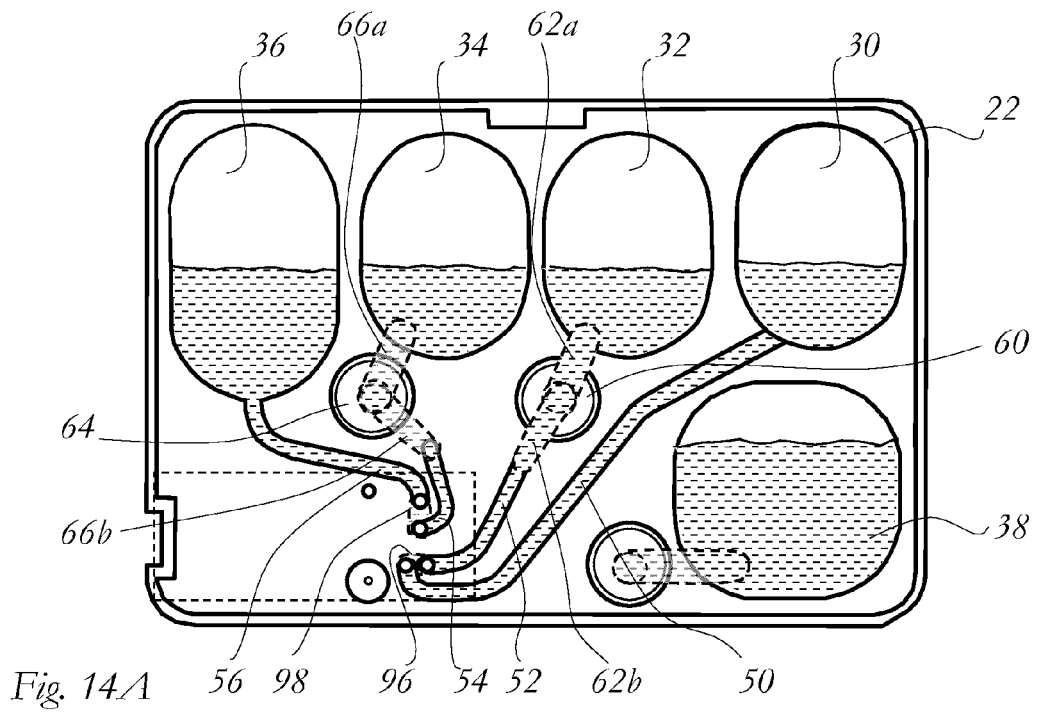

At this time, system control 200 activates pusher 160, which is located within side wall 132a of cassette compartment 130 (see FIG. 9). Pusher 160 pushes sampling sled 80, through pusher opening 29 of cassette 10 (see FIG. 12), from the filling position to the flushing position. As described in detail above, the move of sampling sled 80 from the filling position to the flushing position causes isolation of a first predetermined volume of the blood sample in first sampling cavity 86 and a second predetermined volume of the blood sample in second sampling cavity 88, respectively. Once sampling sled 80 is in the flushing position, pressure actuator assembly 190 moves plungers 194 and 196 forward to apply a pressure again on mixing chambers 32 and 34, as described above and illustrated in FIG. 13. However, this time, the diluent in mixing chamber 32 flows through channel 52, flushes the predetermined volume of the blood in first sampling cavity 86 into channel 50, and carries the blood into mixing chamber 30, as illustrated in FIGS. 6A and 14A. Similarly, the lysing reagent in mixing chamber 34 flows through channel 54, flushes the predetermined volume of the blood in second sampling cavity 88 into channel 56, and carries the blood into mixing chamber 36, see FIGS. 6A and 14A.

Figure 13A:
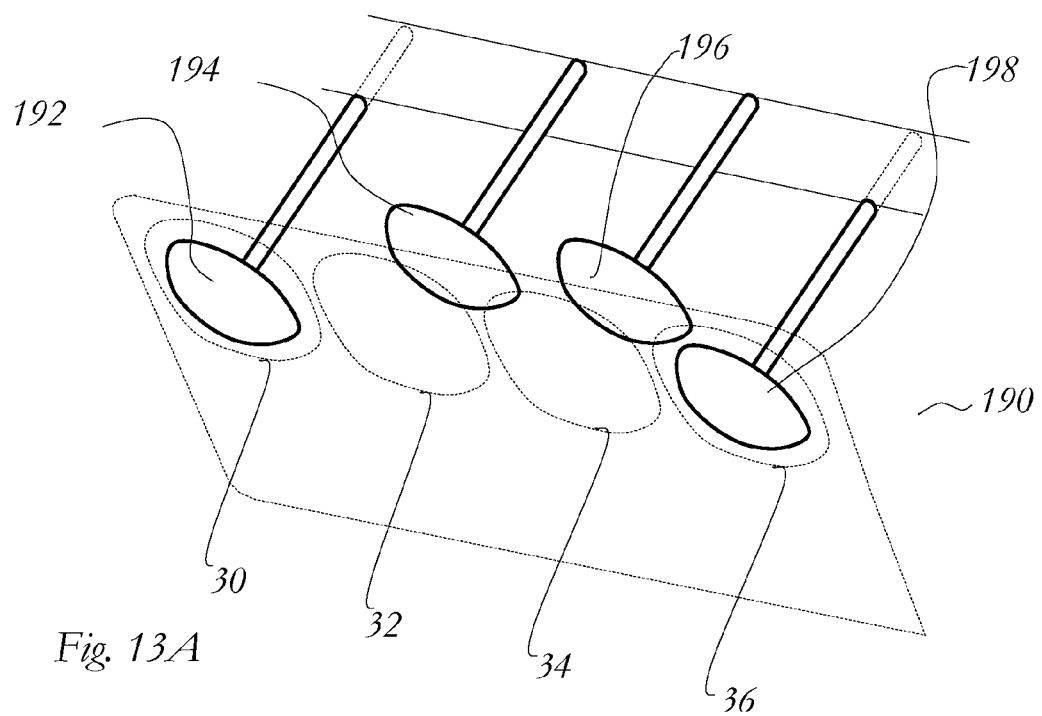

Then, as shown in FIG. 13A, pressure actuator assembly 190 moves plungers 194 and 196 backward, and moves plungers 192 and 198 forward to apply a pressure on mixing chambers 30 and 36. Under the pressure, the mixture of the blood and the diluent in mixing chamber 30 flows to mixing chamber 32 through the path described above, in a reverse direction. Similarly, the mixture of the blood and the lysing reagent in mixing chamber 36 flows to mixing chamber 34 through the path described above, in a reverse direction. The movement of plungers 194, 196 and plungers 192, 198 are alternated several times, which causes the mixture of the blood and the diluent flowing back and forth between mixing chambers 30 and 32, and the mixture of the blood and the lysing reagent flowing back and forth between mixing chambers 34 and 36. This back and forth flow movement provides adequate mixing of the blood with the diluent or the lysing reagent, which produces the first and the second sample mixtures, respectively, for subsequent measurements. It is noted that the priming of the diluent and the lysing reagent prior to flushing the blood out from the sampling cavities is preferred, which prevents a direct contact of the blood on, and potential attachment with, dry surfaces in the flow path, and enhances efficiency of mixing.

After mixing, the first sample mixture (blood and the diluent) is withdrawn from first sample outlet 60 through needle 182 and a first conduit, by a vacuum force, into a first blood measurement device of blood measurement assembly 170 to measure the red blood cells. At the same time, the second sample mixture (blood and the lysing reagent) is withdrawn from second sample outlet 64 through needle 184 and a second conduit, by a vacuum force, into a second blood measurement device of blood measurement assembly 170 to measure the white blood cells and hemoglobin concentration. When the measurements are complete, the cleaning solution in chamber 38 is withdrawn through needle 188 into a separate conduit that is fluidly connected with the first and the second blood measurement devices to clean the devices. The flow system of the blood analyzer is so designed that the cleaning solution pushes the first and the second sample mixture back into the mixing chambers of cassette 10 where they come from. As such, at the end of cleaning, all sample mixtures are returned back to the cassette 10. After the cleaning is complete, cassette interface 180 of blood measurement assembly 170 retrieves from the cassette. At this time, the operator can move cassette receiving interface 120 to the open position, and remove cassette 10 for disposal. Then, a new cassette is placed in the cassette compartment and the process described above is repeated for preparing and measuring another sample.

It is noted after the needles retrieve from the sample outlets and the cleaner outlets, the covers of the outlets made of resilient material seal the outlets from leaking. Moreover, as sampling sled 80 is no longer aligned with filling inlet, the used cassette is self-sealed, and no bio-hazard material leaks from the used cassette.

If another sample is not analyzed on the blood analyzer immediately, the used cassette remains in the cassette compartment and cassette receiving interface 120 remains at its closed position. The system control of the blood analyzer maintains cassette interface 180 at its position during sample analysis. As such, the heads of needles 182, 184, and 188 remain inside sample outlets and cleaner outlets, 60, 64, and 68, respectively, and all needles are immersed in clean cleaning solution that had pushed the used sample mixtures back into the mixing chambers. In the manner, the needles remain wet and no salt crystals or particles form inside and outside the needles. It should be understood that the needles are the front ends of the conduits of the blood measurement devices for blood cell or particle counting. Any particle formation in the conduits may cause error in cell counting and may also cause clogging to the flow path. In this context, it can be appreciated that the sample outlets and the cleaner outlet, in addition to the functions described above, further function as liquid seals of the cassette interface 180 of blood measurement assembly 170. It has been found that using this mechanism, the blood analyzer of the present invention can operate continuously for months without problems resulting from particle contamination from the cassette interface.

The disposable cassette and the blood analyzer described above are particularly suitable for near-patient testing. The method of using the cassette for preparing and measurement of a blood sample, from filling the blood to disposing the cassette, is simple and requires minimum operator training. The disposable cassettes are self-contained, which include the reagents need for preparing a blood sample and the cleaning solution for cleaning the blood analyzer after measurement of a sample. As such, the blood analyzer requires minimum instrument maintenance and separate reagent usage and inventory management.

The disposable cassette and the method of use of the present invention have various advantages over the devices known in the art. In one aspect, a common problem of reagent cassettes known in the art is leaking of the reagents contained in the cassette during storage or transportation. As can be appreciated, the pre-filled diluent and lysing reagent have predetermined volumes, and each reagent volume determines actual dilution ratio of the sample mixture being prepared. The accuracy of the measurement results ultimately depend on the isolated blood volumes and the reagent volumes. Therefore, any leak of the reagents during storage and transportation will cause erroneous measurement results, and potentially affect patient diagnosis. As described above, the disposable cassette of the present invention uses a unique structure of the sample outlets to seal each reagent in one mixing chamber. The reduced reagent contact area and secure sealing, by a molded component structure or its equivalents, prevent reagent leak during storage and transportation. As described above, in prior art devices, sampling valves are also used for separating and sealing the reagents. Substantially different from the prior art devices, in the cassette of the present invention the reagent sealing components are separate from the sampling section. As can be appreciated, until the cassette is placed into the blood analyzer and the needles pierce the membranes within the sample outlets, the diluent and the lysing reagent have no contact with the sampling sled. Therefore, there is no potential risk of chemical contaminations at the sampling section of the cassette. It is noted any lysing reagent in the sampling area could cause lysing of blood cells prior to the blood being mixed with the reagents. As a result, the disposable cassette of the present invention can be reliably used for in-vitro diagnostic analyses.

On the other hand, the divider can be conveniently broken to establish fluid communication among mixing chambers and sampling cavity, by a piecing element which is also a necessary interface for establishing fluid communication between the cassette and the blood analyzer. As such, one piecing element serves two functions. Moreover, as described above, immersing the heads of the needles within sample outlets between sample analyses or during instrument idle time, effectively prevents crystal formation from the reagents used and particle contamination of the instrument.

As a critical issue of particle counting devices using impedance measurements, air bubbles need to be prevented in the sample mixture, since air bubbles can be counted as particles by the impedance measurement devices. The structure of the cassette of the present invention effectively minimizes the possibility of withdrawing air bubbles into the blood measurement devices. As can be appreciated from FIGS. 14 and 14A, at its vertical position where the cassette is engaged with the blood analyzer, both sample outlets are located below the mixing chambers. The liquid level in the mixing chambers, as shown in FIG. 14A, does not descent below the joint interface between a mixing chamber and segment 62a or 66a of the sample outlets. Therefore, any bubbles formed during mixing move to the upper surface of the liquid, and no bubble stays in the sample outlets. When the formed sample mixtures are withdrawn after mixing, the sample mixtures are free of air bubbles.

In a further aspect, as a unique structure of the instant cassette, as described above, diaphragm 39 seals the area above vent opening 75, yet remains a space 72 for releasing air during filling of a blood sample. This externally sealed venting mechanism provides an effective safety measure in preventing upward blood spill from the vent opening, and protects operators from potential threads of bio-hazard materials in clinical environment, particularly in emergency care where the disposable cassette and the blood analyzer of the present invention are intended to be used for. Furthermore, in case of serious overfill, for example, when an operator accidentally uses a 100 µl micropipette, instead of a 20 µl micropipette, to fill the blood, space 72 underneath the diaphragm functions as a buffer zone to absorb the excess amount of blood to prevent blood back spill from the filling inlet. This double prevention mechanism is designed for minimum operator training and skills, which provides a user friendly device and reduces risks in handling bio-hazard materials. Moreover, as the blood sample is filled in from the upper side of the cassette, blood handling and operator's exposure to blood are reduced. The cassette can be placed into the cassette compartment first, a blood can be simply filled using a commercial available micropipette, the door or cassette receiving interface can be closed. The operator does not have further contact with the cassette after blood is filled in, and does not need to handle additional blood filling tools. Furthermore, since diaphragm 39 is transparent, the area above vent opening 75 can also be used for monitoring blood filling. For example, a seriously clogged blood sample, the blood may not flow into the sampling cavity 88. In this situation, a blood sensor disposed in the blood analyzer and directed at the position of vent opening 75 can sense an improper filling and the system control can abort the analysis process. As such, no large particles due to clogged blood sample would be introduced into the flow path of the blood measurement devices, which would be very difficult to remove from the instrument system.

In another aspect, using the disposable cassette of the present invention two sample mixtures for separate measurements of red blood cells/platelets and white blood cells can be prepared concurrently. Both sample mixtures are prepared with one step dilution in the disposable cassette. In comparison, various existing cassettes require multiple steps of dilution to prepare the sample mixtures for red blood cell and white blood cell measurements. The instant cassette saves overall blood measurement time, reduces complexity of the sample preparation process, and improves accuracy of the measurement, because each step of dilution itself involves inherent errors. Moreover, separate dilutions also provide a safe guard for the accuracy of the measurements, because two independent blood isolations and sample preparations can provide additional information on identifying process errors. For example, in a case of a gross error in filling, only 10 μl of a blood is filled into the cassette, and most likely the second sampling cavity 88 is not fully filled. In this case, the white blood cells and hemoglobin measurement results most likely are affected. Consequently, the mean corpuscular hemoglobin concentration (MCHC), a derivative parameter that depends on both red blood cell and the hemoglobin measurements, would reflect the error, because MCHC is typically substantially constant among different blood samples. In such a situation, the error in filling will not be easily identified with the existing double dilution method where a single aliquot of a blood sample is isolated for both red blood cell and white blood cell analyses, as the error in sample isolation will be equally carried in both red blood cell and white blood cell measurements.

Moreover, using the disposable cassette of the present invention, sampling or isolation of two aliquots of predetermined volume of a blood for the red blood cell and white blood cell measurements is accomplished simultaneously in one simple step. The sampling mechanism used in the disposable cassette provides accurate measurement, and a small sample volume, totally no more than 20 μl of a patient's blood is used for a complete blood count (CBC), which provides red cell index, white blood cell count, as well as white blood cell differentiation into at least three subpopulations, such as lymphocytes, granulocytes, and middle population (MID) cells which includes primarily mononuclear cells. The accuracy and precision of these parameters obtained using the disposable cassette and the blood analyzer of the present invention are comparable to existing automated commercial hematology analyzer designed for doctor's offices or small clinical laboratories, which measures blood samples using automated sample aspiration and segmentation by a shearing valve on the instrument and automated sample dilution and mixing using reagents provided on the instrument.

As can be further appreciated, the structure of the disposable cassette of the present invention enables a relatively simple and consolidated interface of the blood analyzer. The upper side of the cassette is used as an interface with the instrument for both mixing and retrieving the sample mixtures, as well as for returning the waste, therefore, the cassette reduces complexity, size, and associated costs of the instrument interface structures.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A disposable cassette for blood analysis comprising:
   a housing having an upper panel with a sampling section;
   at least one pair of chambers in a form of depression of said upper panel of said housing and sealed by a diaphragm, portions of said diaphragm over said chambers being flexible, and one or more channels adapted to interconnect said pair of chambers; one of said chambers containing a predetermined amount of a liquid reagent for said blood analysis; and
   a sample outlet disposed next to and connected to said chamber containing said liquid reagent, said sample outlet comprising an outlet cavity recessed from said upper panel, a cover made of a resilient material sealing said outlet cavity, and a divider within said outlet cavity dividing said outlet cavity into two segments, one of said segments being connected to said chamber containing said liquid reagent, and another of said segments being connected to another chamber of said pair of chambers by said one or more of channels, said divider sealing said liquid reagent to said chamber containing said liquid reagent and isolating said liquid reagent from said sampling section, and said divider being pierceable, wherein when said cassette is used for said blood analysis, said divider is pierced by a piercing element to create an opening therethrough, thereby establishing a fluid communication between said pair of chambers through said outlet cavity.

2. The disposable cassette of claim 1, wherein said divider is a membrane disposed between said two segments of said outlet cavity.

3. The disposable cassette of claim 2, wherein said membrane is an integral part of said housing made by plastic molding.

4. The disposable cassette of claim 2, wherein said membrane has a thickness of about 0.2 to 0.3 millimeters.

5. The disposable cassette of claim 1, wherein said liquid reagent sealed by said divider is isolated from said one or more channels.

6. The disposable cassette of claim 1, wherein said cover is seated in a cover seat recessed from said upper panel of said housing.

7. The disposable cassette of claim 1, wherein said divider is pierced by said piercing element through said cover.

8. The disposable cassette of claim 1 further comprising a cleaner chamber, in a form of depression of said upper panel of said housing and sealed by a diaphragm, containing a cleaning solution therein, and a cleaner outlet disposed next to and connected to said cleaner chamber, said cleaner outlet sealing said cleaning solution to said cleaner chamber.

9. The disposable cassette of claim 1 further comprising a second pair of chambers in a form of depression of said upper panel of said housing and sealed by said diaphragm; portions of said diaphragm over said chambers being flexible; and additional one or more channels adapted to interconnect said second pair of chambers; one of said second pair of chambers containing a predetermined amount of a second reagent for said blood analysis; and a second sample outlet disposed next to and connected to said chamber containing said second reagent, said second sample outlet comprising an outlet cavity recessed from said upper panel and sealed by a cover made of a resilient material and a divider within said outlet cavity, said divider sealing said second reagent to said chamber containing said second reagent and isolating said second reagent from said sampling section, and said divider of said second sample outlet being pierceable, wherein when said cassette is used for blood analysis, said divider of said second sample outlet is pierced by another piercing element to create an opening therethrough, thereby establishing a fluid communication between said second pair of chambers through said outlet cavity of said second sample outlet.

10. The disposable cassette of claim 9, wherein both sample outlets are located on a same side of said pairs of chambers.

11. The disposable cassette of claim 1, wherein said one or more channels are interconnected at said sampling section.

12. A method of using a disposable cassette for blood analysis, said method comprising:

providing a disposable cassette comprising a housing having an upper panel with a sampling section; at least one pair of chambers in a form of depression of said upper panel of said housing and sealed by a diaphragm, portions of said diaphragm over said chambers being flexible, and one or more channels adapted to interconnect said pair of chambers; a first chamber of said pair of chambers containing a predetermined amount of a liquid reagent; and a sample outlet disposed next to and connected to said first chamber, said sample outlet comprising an outlet cavity recessed from said upper panel, a cover made of a resilient material sealing said outlet cavity, and a divider within said outlet cavity dividing said outlet cavity into two segments, one of said segments being connected to said first chamber containing said liquid reagent, and another of said segments being connected to a second chamber of said pair of chambers by said one or more of channels, said divider sealing said liquid reagent to said first chamber and isolating said liquid reagent from said sampling section, and said divider being pierceable;

piercing said divider in said sample outlet by a piercing element to create an opening through said divider, thereby establishing fluid communication between said first chamber and said second chamber through said outlet cavity; and applying a pressure on a portion of said diaphragm over said first chamber, and causing said liquid reagent to flow from said first chamber through said one or more channels to said second chamber.

13. The method of claim 12, wherein flowing of said liquid reagent from said first chamber carries a sample isolated at said sampling section through said one or more channels to said second chamber.

14. The method of claim 13, wherein said method further comprises applying a pressure between said first chamber and said second chamber to cause said liquid reagent and said sample to flow back and forth to affect mixing, thereby obtaining a sample mixture.

15. The method of claim 14, wherein said piercing element is a piecing needle of a blood analyzer, said piercing needle pierces said divider through said cover.

16. The method of claim 15, wherein said method further comprises retrieving an end of said piecing needle from said opening of said divider prior to applying a pressure on said diaphragm, while retaining said end of said piecing needle underneath said cover.

17. The method of claim 16, wherein said method further comprises advancing said piecing needle within said outlet cavity, and withdrawing said sample mixture through said piecing needle to said blood analyzer.

18. The method of claim 17, wherein said method further comprises returning said sample mixture from said blood analyzer, after a measurement, back to said disposable cassette through said piecing needle in said sample outlet.

19. The method of claim 18, wherein said method further comprises withdrawing a cleaning solution contained in a cleaner chamber of said disposable cassette to clean components of said blood analyzer in contact with said sample mixture for said measurement, and returning said sample mixture and said cleaning solution from said blood analyzer back to said disposable cassette through said piecing needle in said sample outlet.

20. The method of claim 18, wherein said method further comprises retrieving said piecing needle from said sample outlet, and disposing used cassette with said sample mixture sealed therein.

* * * * *